(12) United States Patent
Stein et al.

(10) Patent No.: US 11,331,290 B2
(45) Date of Patent: May 17, 2022

(54) NICLOSAMIDE FOR THE TREATMENT OF CANCER METASTASIS

(71) Applicant: Max-Delbrück-Centrum für Molekulare Medizin in der Helmholtz-Gemeinschaft, Berlin (DE)

(72) Inventors: Ulrike Stein, Panketal (DE); Wolfgang Walther, Panketal (DE); Ulrike Sack, Berlin (DE); Peter M. Schlag, Berlin (DE)

(73) Assignee: Max-Delbrück-Centrum für Molekulare Medizin in der Helmholtz-Gemeinschaft, Berlin (DE)

( * ) Notice: Subject to any disclaimer, the term of this patent is extended or adjusted under 35 U.S.C. 154(b) by 0 days.

(21) Appl. No.: 16/775,156

(22) Filed: Jan. 28, 2020

(65) Prior Publication Data

US 2020/0155484 A1    May 21, 2020

Related U.S. Application Data

(63) Continuation of application No. 14/112,521, filed as application No. PCT/EP2012/057049 on Apr. 18, 2012, now abandoned.

(30) Foreign Application Priority Data

Apr. 18, 2011    (EP) ...................................... 1162875

(51) Int. Cl.
| | | |
|---|---|---|
| *A61K 31/167* | (2006.01) | |
| *A61K 31/4035* | (2006.01) | |
| *A61K 45/06* | (2006.01) | |
| *A61P 35/00* | (2006.01) | |

(52) U.S. Cl.
CPC ........ *A61K 31/167* (2013.01); *A61K 31/4035* (2013.01); *A61K 45/06* (2013.01)

(58) Field of Classification Search
CPC .. A61K 31/167; A61K 45/06; A61K 31/4035; A61P 35/00
See application file for complete search history.

(56) References Cited

U.S. PATENT DOCUMENTS

2005/0250709 A1    11/2005    Khodadoust

FOREIGN PATENT DOCUMENTS

| WO | WO 2004/006906 A2 | 1/2004 |
|---|---|---|
| WO | WO 2005/060951 A2 | 7/2005 |
| WO | WO 2011/035321 A1 | 3/2011 |

OTHER PUBLICATIONS

Boye et al., "S100A4 and Metastasis," Feb. 2010, The American Journal of Pathology, vol. 175, No. 2, pp. 528.535.

*Primary Examiner* — Trevor Love
(74) *Attorney, Agent, or Firm* — Knobbe, Martens, Olson & Bear, LLP

(57) ABSTRACT

A method for inhibiting, reducing and/or reducing the risk of cancer metastasis in a subject, including identifying a subject as in need of inhibiting, reducing and/or reducing the risk of cancer metastasis, by identifying the subject as having a cancer with an elevated or up-regulated level of S100A4 transcription compared to a level in non-oncogenic cells, and administering to the subject a therapeutically effective amount of niclosamide or a niclosamide derivate, thereby inhibiting or reducing S100A4 transcription, so as to inhibit, reduce and/or reduce the risk of cancer metastasis, wherein 15 to 400 mg niclosamide or niclosamide derivate is administered per kg body weight of the subject (mg/kg), 1 or 2 times daily.

15 Claims, 23 Drawing Sheets

Specification includes a Sequence Listing.

A

B

SEQUENCE LISTING

<160> NUMBER OF SEQ ID NOS: 10

<210> SEQ ID NO 1
<211> LENGTH: 18
<212> TYPE: DNA
<213> ORGANISM: Artificial sequence
<220> FEATURE:
<223> OTHER INFORMATION: primer

<400> SEQUENCE: 1
ctcagcgctt cttctttc                                                   18

<210> SEQ ID NO 2
<211> LENGTH: 18
<212> TYPE: DNA
<213> ORGANISM: Artificial sequence
<220> FEATURE:
<223> OTHER INFORMATION: primer

<400> SEQUENCE: 2
gggtcagcag ctccttta                                                   18

```
<210> SEQ ID NO 3
<211> LENGTH: 26
<212> TYPE: DNA
<213> ORGANISM: Artificial sequence
<220> FEATURE:
<223> OTHER INFORMATION: primer

<400> SEQUENCE: 3
tgtgatggtg tccaccttcc acaagt                                          26

<210> SEQ ID NO 4
<211> LENGTH: 22
<212> TYPE: DNA
<213> ORGANISM: Artificial sequence
<220> FEATURE:
<223> OTHER INFORMATION: primer

<400> SEQUENCE: 4
tcgggcaaag agggtgacaa gt                                              22

<210> SEQ ID NO 5
<211> LENGTH: 60
<212> TYPE: DNA
<213> ORGANISM: Artificial sequence
<220> FEATURE:
<223> OTHER INFORMATION: probe

<400> SEQUENCE: 5
ccgggcatgg ggatccccac ccagttttt gtttctgaat ctttattttt ttaagagaca      60

<210> SEQ ID NO 6
<211> LENGTH: 60
<212> TYPE: DNA
<213> ORGANISM: Artificial sequence
<220> FEATURE:
<223> OTHER INFORMATION: probe

<400> SEQUENCE: 6
tgtctcttaa aaaataaag attcagaaac aaaaactggg gtggggatcc ccatgcccgg      60

<210> SEQ ID NO 7
<211> LENGTH: 18
<212> TYPE: DNA
<213> ORGANISM: Artificial sequence
<220> FEATURE:
<223> OTHER INFORMATION: primer

<400> SEQUENCE: 7
tgttcccctc cagatccc                                                   18

<210> SEQ ID NO 8
<211> LENGTH: 19
<212> TYPE: DNA
<213> ORGANISM: Artificial sequence
<220> FEATURE:
<223> OTHER INFORMATION: primer

<400> SEQUENCE: 8
ggctatgctc aagccactg                                                  19

<210> SEQ ID NO 9
<211> LENGTH: 22
<212> TYPE: DNA
<213> ORGANISM: Artificial sequence
<220> FEATURE:
<223> OTHER INFORMATION: primer
```

```
<400> SEQUENCE: 9
ccttaatatt cccacacatg gc                                          22

<210> SEQ ID NO 10
<211> LENGTH: 21
<212> TYPE: DNA
<213> ORGANISM: Artificial sequence
<220> FEATURE:
<223> OTHER INFORMATION: primer

<400> SEQUENCE: 10
ctgcgtttgg aagcagaaag t                                           21
```

NICLOSAMIDE FOR THE TREATMENT OF CANCER METASTASIS

FIELD OF INVENTION

Cancer metastasis is often associated with activation of the Wnt/β-catenin signaling pathway and high expression of the metastasis-inducing gene S100A4. It has been demonstrated in the state of the art, that S100A4 is transcriptionally regulated by β-catenin and that this is important for colon cancer and metastasis. The invention relates to niclosamide and derivates thereof, which effectively inhibit transcription of the S100A4 gene, resulting in inhibition of S100A4-induced cell motility, invasiveness, metastasis and proliferation of human cancer cells.

REFERENCE TO SEQUENCE LISTING

A Sequence Listing submitted as an ASCII text file via EFS-Web is hereby incorporated by reference in accordance with 35 U.S.C. § 1.52(e). The name of the ASCII text file for the Sequence Listing is 32099802_1.txt, the date of creation of the ASCII text file is Jan. 28, 2020, and the size of the ASCII text file is 2.12 KB.

BACKGROUND OF THE INVENTION

Over the last decades, the efficacy of cancer treatment has improved considerably. However, clinical outcome parameters in particularly in the metastatic situation, have changed only moderately. Therefore, the development of new approaches to fight cancer is the ultimate goal of scientists as well as of pharmaceutical companies.

Colorectal cancer is one of the most frequent malignant tumors with a still increasing incidence in Western countries. In the United States, this disease accounts for 10% of all cancers, and is currently the second or third leading cause of cancer-related death of men or women, respectively (both sex combined 10%). In Europe, colorectal cancer was the second most common cancer both in terms of incidence (376.400 cases, 13%) and mortality (203.700 death, 12%) in 2004. In Germany, colorectal cancer was also listed among the 20 most frequent causes for cancer deaths in 2003, with 18% in men second after lung cancer, and with 11% in women, following breast and lung cancer (www.dkfzheidelberg.de). More than 70,000 individuals suffered from colorectal cancer in 2007 in Germany, and 30,000 died of this disease (http://www.aerztezeitung.de). It was calculated, that about 6% of the German population, which equals about 5 million people, will suffer from colorectal cancer in the course of their life time. Thus, increased efforts for understanding, prevention, and intervention of that disease are extremely desired.

Today, colorectal cancer and metastasis thereof are understood as the results of early changes during tumor progression which determine the metastasis capacity. The genetic abnormalities occurring during neoplastic transformation are essential for the cancer to arise and most of abnormalities take place early in the disease process but none of the abnormalities are known to be specifically associated with metastasis. This 'change of state' (=metastasis), when cancer spreads from its primary site to secondary sites in the body is one of the hallmarks of cancer. The seeding and growth of satellite lesions in other organs is responsible for greater than 90% of neoplastic deaths. Primary tumours can normally be removed by surgery but widely metastatic lesions are difficult to detect and difficult or impossible to treat with adjuvant therapies. Metastasis is a multi-step process, involving loss of cell adhesion, increased cell motility, invasion of the surrounding tissue, intravasation of blood vessels or the lymphatic system to enter the circulatory system, extravasation from the circulatory system, proliferation at a new secondary site, and building of a vascular system to support growth. The capability of a tumour to facilitate metastasis is acquired through changes in gene expression and the microenvironment.

Much is known about molecules contributing to the metastasis phenotype, about pathways they control, and about genes they regulate. Molecular-based staging as essential prerequisite for improved diagnosis, prognosis and therapy, since patient prognosis today is still mainly defined by histopathological staging, a static description of the anatomical extent of tumor spread within a surgical specimen. Molecular determinants for progression and metastasis of colorectal cancer represent both, markers for metastasis prognosis, and targets for intervention strategies aiming at the ultimate goal of metastasis prevention.

Colorectal cancer is often associated with activation of the Wnt/β-catenin signaling pathway and high expression of the metastasis-inducing gene S100A4. In addition to its function in the cell-cell adhesion, β-catenin is also an important mediator of the canonical Wnt signalling pathway. When no Wnt signalling occurs, two scaffolding proteins, the tumour suppressor APC and AXIN, form the so-called destruction complex with β-catenin, which facilitates the sequential phosphorylation of β-catenin by CKI and GSK3-β at the amino-terminus. The phosphorylations recruit the F box/WD repeat protein β-TrCP-containing E3 ubiquitin ligase, which marks β-catenin for proteosomal degradation. Wnt signalling pathway is activated by binding of the Wnt ligand to the Frizzled transmembrane receptor, a serpentine receptor with a amino-terminal cysteine-rich domain. The complex then interacts with a single-pass transmembrane protein of the LDL receptor family (LRP5/6). It is not clear how the FRZ/LRP complex regulates the kinase activity of the destruction complex. However, it is suggested that the activity axin/GSK3-3 is inhibited by a mechanism involving the interaction of axin with LRP5/6 or the action of the axin binding molecule Dishevelled (DSH). The unphosphorylated β-catenin translocates to the nucleus where it binds to the amino-terminus of the Tcf/Lef (T cell factor/lymphoid enhancer factor) family of DNA-binding proteins and activates the transcription of target genes. The Tcf/Lef proteins repress target genes in the absence of β-catenin, but transform into transcriptional activators once they bind to β-catenin.

The relevance of the Wnt pathway for cancer cells is indicated by the high percentage of mutations occurring in the genes of the Wnt pathway. For example, over 90% of colorectal cancers bear mutations that result in Wnt pathway activation. These mutations generally affect β-catenin phosphorylation and stability, hindering its degradation via the ubiquitin pathway. Nonphosphorylated β-catenin accumulates in the cytoplasm, is transported to the nucleus, and interacts with TCF family transcription factors to control target genes. Nuclear β-catenin accumulation has been associated with late stages of tumor progression and development of metastases, and the presence of mutated β-catenin is associated with aggressive tumor growth and poor prognosis.

One major target that is linked to metastasis formation is S100 calcium binding protein A4 (S100A4), an 11 kDa protein, originally identified as metastasin 1(MTS1).

S100A4 is overexpressed in many different types of cancer such as gallbladder, bladder, breast, esophageal, gastric, pancreatic, hepatocellular, non-small cell lung and especially colorectal cancer. Increased expression of S100A4 is strongly associated with aggressiveness of a tumor, its ability to metastasize and poor survival in patients. However, S100A4 itself is not tumorigenic because transgenic mice overexpressing S100A4 do not develop tumors per se. But, when S100A4 transgenic mice are crossed with mice demonstrating spontaneous tumor formation, it leads to aggressive tumor growth and metastasis. Moreover, S100A4-null mice injected with highly metastatic mouse mammary carcinoma cells show no metastases. These observations suggest that S100A4 is essential for the process of metastasis formation.

S100A4 plays a major role in cellular processes such as migration, invasion, adhesion and angiogenesis, which form the basis for metastasis formation. For instance, S100A4 increases cell motility by interacting with proteins from the cytoskeleton, such as the heavy chain of non-muscle myosin II (MYH9). Moreover, S100A4 participates in cell adhesion by interaction with protein tyrosine phosphatase receptor type F (PTPRF) interacting protein, binding protein 1 (PP-FIBP1; also known as liprin β-1) and promotes cell invasion and angiogenesis via upregulation of metallomatrix peptidase (MMPs).

Despite intensive research revealing the manifold roles of S100A4, no inhibitor of S100A4 expression has been described thus far that inhibits S100A4-mediated metastasis.

SUMMARY OF THE INVENTION

In light of the prior art the technical problem underlying the present invention is to provide an inhibitor of cancer metastasis.

This problem is solved by the features of the independent claims. Preferred embodiments of the present invention are provided by the dependent claims.

The invention therefore relates to the use of niclosamide and derivates thereof for the inhibition and/or reduction of the spread of metastatic cancer, especially cancer cell migration and invasion.

A high-throughput screening of 1280 small molecules was performed in order to identify inhibitors of S100A4 promoter-driven reporter gene expression with potential clinical anti-metastatic activity. A highly effective substance—niclosamide—was identified, which is an approved anti-helminthic drug for treatment of tapeworm infections. Surprisingly, niclosamide has a strong effect on the expression of S100A4 by inhibiting its transcription. Furthermore, niclosamide can be used to inhibit S100A4-induced cell migration and invasion as well as cell proliferation and colony formation in vitro.

Cell migration, especially directed cell migration contributes to pathologies including vascular disease, chronic inflammatory diseases, and tumor formation and metastasis. Migration is a dynamic, cyclical process in which a cell extends a protrusion at its front, which in turn attaches to the substratum on which the cell is migrating. This is followed by a contraction that moves the cell body forward toward the protrusion, and finally the attachments at the cell rear release as the cell continues to move forward. The cycle is initiated by external signals (chemotactic molecules), which are sensed and communicated to the cell's interior by specialized receptive proteins in the cell membrane. In response to these signals, cells extend protrusions, by polymerizing actin, seeking out new terrain and sensing the direction from which they are receiving signals. Once the direction for movement is established the machinery for enabling movement assembles with regard for the direction of migration. Adhesive complexes needed for traction collect at the front of the protrusion, tethering the protrusion to the substratum. Actomyosin filaments contract at the front of the cell and pull the cell body toward the protrusion. Release of adhesive connections in the rear of the cell and retraction of the tail completes the cycle. The orchestration of this complex process resides in many molecules that serve to distinguish the front from the rear of the cell and whose actions are carefully timed. It was very surprising that the addition of niclosamide or derivatives thereof to migrating or invading cells inhibits both processes, especially if the processes are S100A4 driven.

Niclosamide is a chlorinated salicylanilide pesticide principally used against aquatic vertebrates and crustaceans. It is an anthelmintic effective in the treatment of diphyllobothriasis, diphyllobothriasis, hymenolepiasis. It is used to treat broad tapeworms (or fish, dwarf and beef).

Anthelmintic is especially a chemical substance used to expel or destroy tapeworms in domestic animals.

It has been shown, that none of several derivates of niclosamide were effective as niclosamide. Preferably niclosamide is chosen from the group comprising the formulas:

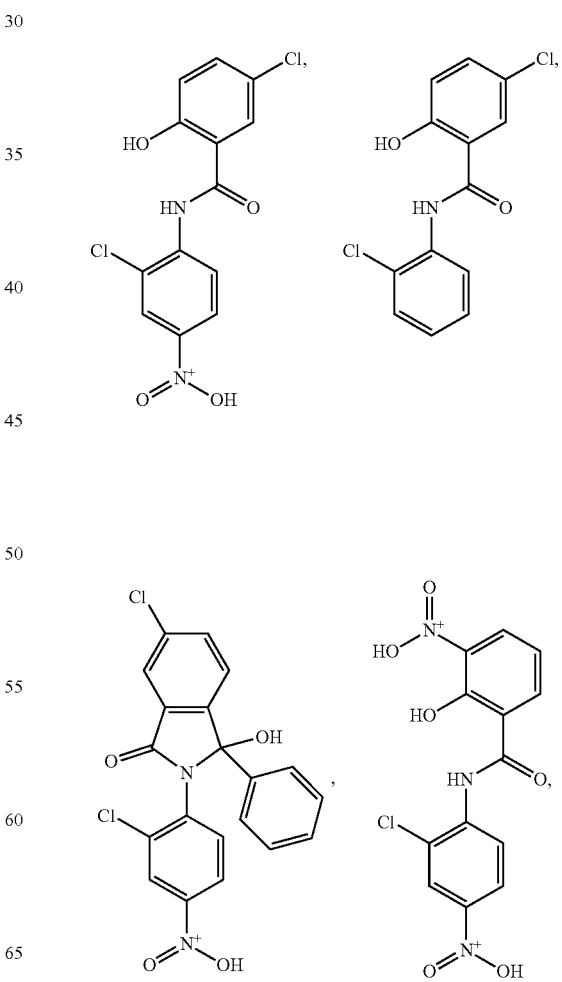

-continued

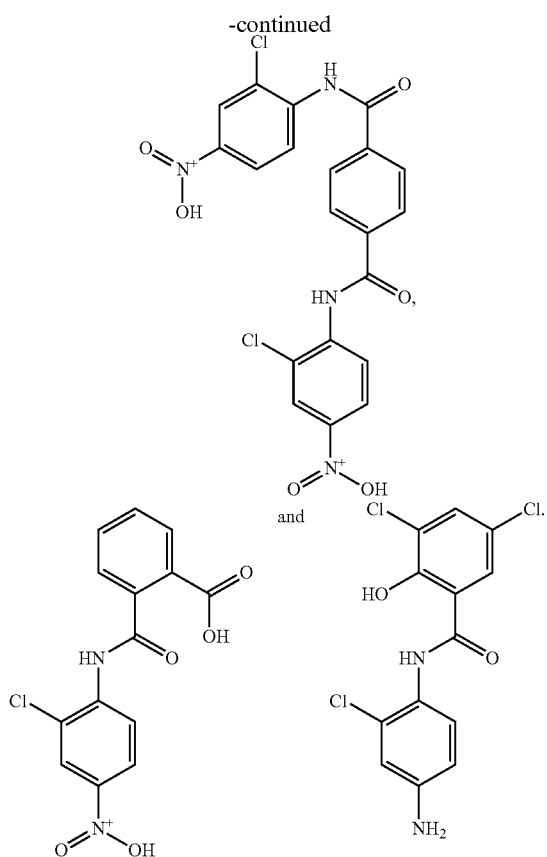

and

However, various derivates of niclosamide have been shown to be effective on S100A4-driven cell migration, invasion and metastasis. The person skilled in the art knows various chemical methods and techniques to render a chemical substance to generate a derivate, which still comprises the chemical basis, such as addition, deletion or substitution of a group or functional group. Niclosamide is also known as 2',5-dichloro-4'-nitrosalicylanilide, 2-Hydroxy-5-chloro-N-(2-chloro-4-nitrophenyl)benzamide, 5-Chloro-2'-chloro-4'-nitrosalicylanilide, 5-Chloro-N-(2-chloro-4-nitrophenyl) salicylamide, Bayluscid, 5-Chloro-N-(2-chloro-4-nitrophenyl)-2-hydroxy Benzamide, Dichlosale, Cestocid or Devermine.

Niclosamide and derivates thereof can be applied in vitro or in vivo to cancer cells, in order to inhibit S100A4-driven cell migration, invasion and metastasis. Cancers are preferably classified by the type of cell that the tumor resembles and is therefore presumed to be the origin of the tumor. These types include:
  Carcinoma: Cancer derived from epithelial cells. This group includes many of the most common cancers, including those of the breast, prostate, lung and colon.
  Sarcoma: Cancer derived from connective tissue, or mesenchymal cells.
  Lymphoma and leukemia: Cancer derived from hematopoietic (blood-forming) cells.
  Germ cell tumor: Cancer derived from pluripotent cells. In adults these are most often found in the testicle and ovary.
  Blastoma: Cancer derived from immature "precursor" or embryonic tissue.

In a preferred embodiment, the cancer is chosen from the group comprising breast cancer, colon cancer, ovarian carcinoma, osteosarcoma, cervical cancer, prostate cancer, lung cancer, synovial carcinoma, melanoma, skin, pancreatic cancer, or other cancer yet to be determined in which S100A4 levels are elevated, up-regulated, mutated or altered in physiology compared to non-oncogenic cells. The cancer can be chosen from S100A4-related cancers. The cancer can be caused by chemicals, infections, radiation, genetic abnormalities, physical trauma and inflammation and physical agents. It was very surprising, that niclosamide is very effective inhibiting the migration, invasion and metastasis of various cancers, in which S100A4 is preferably overexpressed. In the light of the invention, overexpression especially refers to excessive expression of a gene by producing too much of its effect or product, wherein product preferably refers to protein or RNA.

Niclosamide effectively inhibits the expression of S100A4, wherein it affects the transcription of the S400A4 gene or the translation of the mRNA into protein. It is preferred that niclosamide or derivates thereof modulates the TCF/beta-catenin protein complex in a cancer cell. The S100A4 gene is preferably a target of the Wnt pathway and its expression is activated by transcription factors, preferably the transcription complex TCF/beta-catenin.

The modulation of the preferred transcription complex TCF/beta-catenin results in a stop or inhibition of the transcription of the S400A4 gene.

The invention further relates to a method of treatment of a tumour cell which comprises administering to a subject in need or treatment an effective amount of niclosamide or a derivate thereof.

In a preferred embodiment, the subject is preferably a human subject. It is preferred that administering the niclosamide or a derivate thereof inhibits or reduces the expression of S100A4, by preferably modulating a protein complex comprising the transcription factors TCF and beta-catenin.

In a preferred embodiment, S100A4 expression and the spread of metastatic cancer cells is further reduced or inhibited by means of nucleic acid molecules, preferably through nucleic acids with complementarity to mRNA of components of the Wnt pathway. Methods for the inhibition, blocking, suppression, activation or over-expression of a gene are known to one skilled in the art. For example blocking or suppression of an expression of a gene could be carried out via an antibody targeting the translated protein, genetic modification of the cell, such as deletions or other targeted mutations, or the use of anti-sense RNA approaches, such as siRNA or miRNA, in order to silence the protein before translation of its mRNA. However, it could also be preferred to activate or overexpress a component of the Wnt pathway. The activation or over-expression could be achieved via administration of active protein to the cell or by overexpression of the particular protein in an expression vector, or by transformation of any other exogenous nucleic acid coding for the protein to be increased.

The invention also relates to a pharmaceutical composition comprising niclosamide or a derivate thereof for the inhibition of cancer metastasis.

In a preferred embodiment, the pharmaceutical composition comprises at least one niclosamide or a derivate thereof with a pharmaceutically acceptable carrier, wherein said composition is a capsule, a tablet, a coated tablet, a suppository, an ointment, a cream, an injection solution and/or an infusion solution.

It is preferred that in cancer cells niclosamide treatment inhibits CTNNB1/TCF complex formation and thereby interrupts target gene transcription.

In another preferred embodiment, the pharmaceutical composition used, comprises a pharmaceutically tolerable carrier which is selected from the group comprising fillers, disintegrants, binders, humectants, extenders, dissolution re-tarders, absorption enhancers, wetting agents, adsorbents and/or lubricants. As a result, the pharmaceutical composition can be adjusted to the specific requirement of various cancer diseases.

In another preferred embodiment, the above described use of the pharmaceutical composition comprises niclosamide or derivates thereof and one or more chemotherapeutic drug. Chemotherapeutic drugs can be divided into alkylating agents, antimetabolites, anthracyclines, plant alkaloids, topoisomerase inhibitors, and other antitumour agents. All of these drugs affect cell division or DNA synthesis and function in some way.

The advantages like inexpensiveness, clinical efficacy and low exertion of side-effects are evident in another preferred embodiment of niclosamide or derivates thereof, including the method of treating cancer, preferably cancer metastasis in a mammal comprising the administration of an therapeutically effective amount of the composition to the mammal in need of such treatment. It is preferred that the mammal is a human being.

In a preferred embodiment all potential sites of cancer metastasis can be effectively reached, as the above-described method of treatment comprises a route of administration of the pharmaceutical composition that is selected from the group comprising oral, parenteral, intravenous, intra-arterial, pulmonary, mucosal, topical, transdermal, subcutaneous, intramuscular, rectal, intracranial, intracerebroventricular, intracerebral, intravaginal, intrauterine, intrathecal or intraperitoneal administration.

A specifically preferred embodiment comprises the above-described method, wherein the route of administration of the compound is selected from oral and parenteral administration. This embodiment allows the effective treatment of metastasis by the application of different ways of compound delivery. Subcutaneous infections for example can be reached immediately via the bloodstream by intravenous application or minimally invasive by oral application or via the interstitial fluids by subcutaneous injection. Together, these different methods of application offer the possibility to antagonize any cancer metastasis via the optimal way of compound delivery.

The invention also relates to niclosamide or derivates thereof for the treatment of cancer metastasis.

In a preferred embodiment the invention relates to the treatment of a group of patients that are identified by increased expression of S100A4, preferably whereby the cancerous cells show increased expression of S100A4. S100A4 expression can be determined using any commonly known method in the art, such as RT-PCR for analysis of increased expression of S100A4 transcript or immunological based methods such as western blot or ELISA for detection of increased expression of S100A4 protein, or any other diagnostic tools that can provide relative measurements of S100A4 expression in comparison to "normal" or "healthy" or "low risk" cells.

Therefore a preferred embodiment relates to Niclosamide or derivatives thereof for the treatment of prevention of metastasis of cancerous cells in a patient or group of patients identified by increased expression of S100A4, wherein a body fluid and/or a tissue of a patient to be identified is analysed to determine S100A4 expression levels. Body fluids may include aqueous humour and vitreous humour, bile, blood, blood serum, blood plasma, breast milk, cerebrospinal fluid, cerumen (earwax), endolymph and perilymph, gastric juice, mucus (including nasal drainage and phlegm), peritoneal fluid, pleural fluid, saliva, sebum (skin oil), sweat, tears, vaginal secretion, vomit or urine.

The treatment of this particular patient group with niclosamide represents a novel medical use of niclosamide that has been neither suggested nor disclosed in the prior art. The novel effect of niclosamide upon which the invention is based represents a novel technical effect that enables a novel medical use of niclosamide. The identification of the working mechanism of niclosamide with relation to inhibition of S100A4 expression enables niclosamide treatment that has a direct effect on S100A4 gene expression. This direct link between S100A4 expression and niclosamide treatment has not been previously proposed or suggested in the prior art. The knowledge of the direct effect of niclosamide on S100A4 expression allows dosage regimes that are precisely fitted to the patient needs, thereby enabling administration directly to affected areas of the body in amounts that have a relevant effect without providing unwanted side effects. This treatment can for example be carried out by direct treatment of colorectal cancer in the colon of suffering subjects, thereby providing an effective prevention of metastasis. Oral application is also preferred due to low toxicity after systemic administration.

S100A4 expression in tumors from colon cancer patients was shown to be prognostic for the development of metastases. Furthermore, it was recently shown in the state of the art, that quantitative S100A4 transcript determination in plasma of colon cancer patients is prognostic and diagnostic for early cancer staging and defining of patients at high risk for S100A4-induced metastases. Niclosamide is however a novel inhibitor of CTNNB1/TCF interaction that impairs S100A4-induced metastasis, which has not previously been proposed in combination with S100A4.

The medical application of niclosamide to prevent and/or reduce S100A4 expression and thereby prevent metastasis represents a novel combination between medical indication (metastasis prevention) and product (niclosamide) linked by a novel technical effect (prevention and/or inhibition of S100A4 expression) that is unpredictable in light of the known uses of niclosamide and previously known S100A4 function. This novel technical effect also leads to unexpected benefits, such as enhanced survival of patients treated with the substances of the present invention, in addition to low S100A4 levels even long times (weeks) after treatment has finished. It was unexpected, that niclosamide treatment via direct inhibition of S100A4 expression would provide extended prevention of metastasis and cancer cell migration.

The invention therefore also comprises niclosamide and derivatives thereof for the treatment of cancer metastasis, including the inhibition and/or reduction of already existing metastases, and/or for the prevention of cancer metastasis formation. In a preferred embodiment he niclosamide or derivative according to the invention can be applied in therapeutically effective doses to a patient at risk of metastasis occurring, for example a patient already undergoing treatment for any cancer-related condition where metastasis may arise.

DETAILED DESCRIPTION OF THE INVENTION

The invention describes the identification of small molecule inhibitors (niclosamide and derivates thereof), which significantly reduce S100A4 expression especially in colorectal carcinoma cells and specifically interfere with S100A4-driven cell migration and invasion.

A high-throughput screening is presented that identified the anti-helmithic small molecule niclosamide as transcriptional inhibitor of S100A4 expression forming the basis for its novel anti-metastatic action. It is shown that especially in colon cancer cells niclosamide inhibited WNT/CTNNB1 pathway signaling. Thereby, it blocked S100A4 expression in a concentration- and time-dependent manner. Niclosamide treatment impaired S100A4-induced cell migration and invasion and diminished cell proliferation and colony formation in vitro. Consistently, colon cancer xenograft mice presented a clear reduction of S100A4 expression levels within the tumor tissue when mice were treated with niclosamide or derivates thereof. Moreover niclosamide treatment, even when discontinued after 24 days resulted in substantially fewer and smaller liver metastases in xenograft mice.

The high-throughput screening aimed at the identification of S100A4 transcription inhibitors. For that, HCT116-S100A4p-LUC cells as human colon cancer model were used, since these cells bear a constitutively active WNT signaling pathway because of monoallelic CTNNB1 mutation. Thus, these cells show an endogenously elevated S100A4 promoter activity allowing constant reporter gene expression. Screening of 1280 compounds of the LOPAC Library identified niclosamide as the most promising inhibitor of S100A4 expression for in vivo testing.

Niclosamide is an anti-helminthic drug which can be hydrolytically cleaved by cells of the gastrointestinal tract. Metabolism of niclosamide by tumor cells might explain that inhibition of the S100A4 expression was disrupted by even small changes of the niclosamide structure. Variation in aqueous solubility may be an additional factor underlying this initial structure-activity result.

The S100A4 decreasing effect of a single dose of niclosamide was confined to a 24 hours time frame. However, this time frame could be prolonged by applying daily doses of niclosamide achieving a constant reduction of S100A4 expression in vitro and in vivo. Once this level was reached, the niclosamide induced S100A4 suppression along with inhibition of cell motility and proliferation remained stable even after niclosamide treatment was discontinued.

Inhibition of S100A4 expression by shRNA experiments or overexpression of endogenous inhibitors such as PLA2G2A phospholipase or interferon-γ (IFN-γ) results in reduced cell motility and invasiveness. Consistent with this result, niclosamide treatment of e. g. colon cancer cells led to decreased cell migration as well as invasion. The inhibitory effect of niclosamide on cell motility could be overcome by ectopic overexpression of S100A4. These observations again emphasize the central role of S100A4 in cell motility leading to colon cancer metastasis.

It was previously observed in RNAi experiments that depression of S100A4 levels resulted in a G2/M arrest of pancreatic cancer cells and suppressed proliferation rates in gastric cancer cells. It was shown, that niclosamide treatment resulted in a reduction of S100A4 expression and simultaneously a reduction in cell proliferation. However, those two effects seemed to be independent, since ectopic overexpression of S100A4 could not overcome the antiproliferative effect of niclosamide.

Mutation of the WNT pathway is a fundamental step for colon cancer development leading to constitutive pathway activity and target gene expression. WNT pathway activity plays a central role in colon homeostasis. Interference with this pathway therefore bears the risk of unwanted side effects. Niclosamide as a Food and Drug Administration (FDA)-approved drug is used in the clinic to treat helmintosis where it proved to have only slight side effects in humans when taken orally. In xenograft mouse models it was found that non-toxic concentrations were effective in reducing the S100A4 expression level within the tumor tissue and substantially reducing liver metastasis. Interestingly, the inhibitory action of discontinued niclosamide treatment in vivo was nearly as strong as found in mice continuously treated with niclosamide. Despite discontinuation of niclosamide treatment, the S100A4 expression in the spleen tumor as well as the formation of liver metastases was inhibited for another 26 days after treatment discontinuation. Moreover, discontinued niclosamide treatment still had a major effect on the prolongation of overall survival.

The term "nucleic acids" refers a nucleic acid DNA or RNA molecule, either single or double-stranded, as is commonly understood by one skilled in the art. Preferred nucleic acids of the present invention refer to DNA expression vectors, plasmids, RNA molecules.

The term "exogenous nucleic acids" refers to any nucleic acid that does not originate from the cell into which it has been transformed. The nucleic acid sequence may be contained within the genome of the organism into which the nucleic acid molecule is transformed. However, the nucleic acid molecule itself must be transformed into the target cells, thereby originating from an external source. Such exogenous nucleic acids may be synthetic in nature, be produced recombinantly or be purified or extracted from other organisms, or stem from any other source external to the cell to be transformed. In the present invention the exogenous nature does not necessarily refer to the sequence of the nucleic molecule but to its origin. The molecule which is then encoded by the nucleic acid can therefore be a protein or peptide also encoded for by the genome of the recipient cell.

The introduction of exogenous nucleic acids can be carried out via transfection, transduction, transformation or any other process of genetic modification or transformation. This can take place naturally, as occurs when a virus infects cells, or artificially. Methods of artificial transfection include but are not limited to chemical methods, including calcium phosphate precipitation, DEAE-dextran complexation and lipid-mediated DNA transfer; physical methods, including electroporation, microinjection, and biolistic particle delivery (gene gun); and using recombinant, lab manipulated viruses as vectors.

The term "transformation" relates to the bringing of exogenous nucleic acids into the cell via either natural or chemical methods.

The term "derivative" refers to any change of a base compound defined in the present application. The term "derivative" is used to describe a compound which can be an effective agent itself/in its own right or in the derivatised form. Preferred derivates are those provided in FIG. 5A. Further derivatization at each of the modified residues is known to one skilled in the art and further derivates are therefore encompassed in the present invention. For example, further halogens at the various positions occupied by Cl are obvious derivates that are included in the scope of the present invention.

As used herein "pharmaceutical composition" means a composition comprising niclosamide o a derivate thereof whereby the composition can be safely and effectively used as a product to obtain or achieve a desired outcome. The term "pharmaceutical composition" as used herein means compositions which result from the combination of individual components which are themselves pharmaceutically acceptable. For example, where intravenous administration is foreseen, the components are suitable or acceptable (in both quality and quantity) for intravenous administration. Niclosamide or derivates thereof can be administered to mammals, namely humans, by numerous routes, such as intravenously, subcutaneously or intramuscularly. The dose administered may be understood by a person of ordinary skill in the art to be therapeutically effective as a therapy to treat or prevent symptoms of cancer, namely metastasis.

The disclosure presented herein is directed towards a pharmaceutical composition which can be administered through a variety of routes including orally, intraperitoneally, intravenously, subcutaneously, intramuscularly or directly into or onto the affected individual. When the pharmaceutical composition is delivered via an injection, the injection of niclosamide or a derivate thereof can occur as a single injection or multiple injections at any location inside or outside the body and the injection(s) can occur in a single day or over multiple days. The daily dose is administered to a subject wherein the daily amount of niclosamide delivered to the subject from the pharmaceutical composition is about that which is therapeutically effective for treating symptoms associated with cancer, especially metastasis. Additionally, the pharmaceutical composition may optionally include additional components such as salts, stabilizers and antimicrobials without departing from the spirit and scope of the claimed invention. The pharmaceutical composition of the present invention contains niclosamide or derivates thereof and a pharmaceutically acceptable carrier.

The quantity and nature niclosamide or derivates thereof to be incorporated in the composition will vary depending on desired therapeutic effect and the time span for which the composition is to provide a therapeutic effect. The quantity niclosamide or derivates thereof in the pharmaceutical composition is that which will deliver a therapeutically effective amount for treating symptoms associated with cancer, especially metastasis. Of course, the concentration and character niclosamide or derivates thereof to be included in the pharmaceutical composition will vary depending upon the components used in the composition, the route by which it is administered, the symptoms and details of the cancer which requires treatment as well as other factors known to those of skill in the art.

The terms "patient" or "person" are used interchangeably herein, and refer to a mammal, including, but not limited to, primates, including simians and humans.

As used herein, the terms "treatment", "treating" and the like, refer to obtaining a desired pharmacologic and/or physiologic effect. The effect may be prophylactic in terms of completely or partially preventing a cancer metastasis and/or may be therapeutic in terms of a partial or a complete cure for the cancer metastasis and/or adverse affect attributable to the disease. "Treatment" as used herein, covers any treatment of a disease in a mammal, particularly in a human, and includes: (a) preventing the disease from occurring in a subject which has cancer; (b) inhibiting the disease, i.e., arresting its development and metastasis; and (c) relieving the disease, i.e., causing regression of the disease.

As used herein, the term "treatment" is further defined as the application or administration of one or more niclosamide-encompassing compounds or pharmaceutical compositions of the present invention to a subject, where the subject has cancer as noted elsewhere herein, symptoms associated with cancer, where the purpose is to cure, heal, alleviate, relieve, alter, remedy, ameliorate, improve, or affect the cancer, preferably cancer metastasis.

However, "therapeutic" and "prophylactic" treatments are to be considered in their broadest context. The term "therapeutic" does not necessarily imply that a subject is treated until total recovery. Similarly, "prophylactic" does not necessarily mean that the subject will not eventually develop symptoms that are associated with cancer metastasis.

Accordingly, therapeutic and prophylactic treatment includes amelioration of the symptoms of a particular condition or preventing or otherwise reducing the risk of developing a particular condition. The term "prophylactic" may be considered as reducing the severity or the onset of a particular condition, preferably metastasis. "Therapeutic" may also reduce the severity of an existing condition.

The terms application and administration are used synonymously herein and refer to the use of a pharmaceutical composition or compound in order to treat a patient.

The term "effective dosage" as used herein, refers to the amount of an active ingredient high enough to (a) prevent the disease from occurring in a subject which may have cancer; (b) inhibit the disease, i.e., arrest its metastasis; and (c) relieve the disease, i.e., to cause the regression of metastasis, but low enough to avoid serious side effects. What is a safe and effective amount of the active ingredient will vary with the specific galenic formulation, the chemical composition and other like factors.

As used herein, "carrier" includes any and all solvents, dispersion media, vehicles, coatings, diluents, antibacterial and antifungal agents, isotonic and absorption delaying agents, buffers, carrier Solutions, suspensions, colloids, and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

Physiologically tolerable carriers are well known in the art. Exemplary of liquid carriers are sterile aqueous solutions that contain no materials in addition to the active ingredients and water, or contain a buffer such as sodium phosphate at physiological pH value, physiological saline or both, such as phosphate-buffered saline. Still further, aqueous carriers can contain more than one buffer salt, as well as salts such as sodium and potassium chlorides, dextrose, propylene glycol, polyethylene glycol and other solutes. Liquid compositions can also contain liquid phases in addition to and to the exclusion of water. Exemplary of such additional liquid phases are glycerin, vegetable oils such as cottonseed oil, organic esters such as ethyl oleate, and water-oil emulsions. A therapeutic composition contains niclosamide or a derivate thereof of the present invention.

The oral bioavailability of niclosamide is preferably 10%, thus oral treatment of mammals with a dose of 50 mg/kg-400 mg/kg, preferably 100 mg/kg-350 mg/kg, most preferably 150-300 mg/kg of niclosamide is possible, the substance could also be applied intraperitoneally. According to studies by the WHO, mice chronically feeded with 200 mg/kg showed no adverse effects in a total period of two years observation time. Concluding from these studies, the long-term administration of niclosamide does not have severe adverse side effects in healthy animals. This represents a significant benefit to the application of niclosamide in treating and preventing metastasis, as it can be administered in relatively high doses without adverse effects.

The phrase "pharmaceutically acceptable" refers to molecular entities and compositions that do not produce an allergic or similar untoward reaction when administered to a patient.

The term "pharmaceutically acceptable carrier" as used herein means any material or substance with which the active ingredient (niclosamide or a derivate thereof) is formulated in order to facilitate its application or dissemination to the locus to be treated, for instance by dissolving, dispersing or diffusing the said composition, and/or to facilitate its storage, transport or handling without impairing its effectiveness. The pharmaceutically acceptable carrier may be a solid or a liquid or a gas which has been compressed to form a liquid, i.e. the compositions of this invention can suitably be used as concentrates, emulsions, solutions, granulates, dusts, sprays, aerosols, suspensions, ointments, creams, tablets, pellets or powders.

The compound or pharmaceutical composition disclosed herein that contains the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions or compound and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and further disintegrating agents besides niclosamide or derivates thereof, for example corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,166,452; and U.S. Pat. No. 4,265,874, to form osmotic therapeutic tablets for control release. A pharmaceutical composition may also, or alternatively, contain one or more drugs, which may be linked to a modulating agent or may be free within the composition. Virtually any drug may be administered in combination with niclosamide or derivates thereof disclosed herein and an additionally modulating agent, for a variety of purposes as described below. Examples of types of drugs that may be administered with niclosamide or derivates thereof and a modulating agent include analgesics, anesthetics, antianginals, antifungals, antibiotics, anticancer drugs (e.g., taxol or mitomycin C), antiinflammatories (e.g., ibuprofen and indomethacin), anthelmintics, antidepressants, antidotes, antiemetics, antihistamines, antihypertensives, antimalarials, antimicrotubule agents (e.g., colchicine or vinca alkaloids), antimigraine agents, antimicrobials, antipsychotics, antipyretics, antiseptics, anti-signaling agents (e.g., protein kinase C inhibitors or inhibitors of intracellular calcium mobilization), antiarthritics, antithrombin agents, antituberculotics, antitussives, antivirals, appetite suppressants, cardioactive drugs, chemical dependency drugs, cathartics, chemotherapeutic agents, coronary, cerebral or peripheral vasodilators, contraceptive agents, depressants, diuretics, expectorants, growth factors, hormonal agents, hypnotics, immunosuppression agents, narcotic antagonists, parasympathomimetics, sedatives, stimulants, sympathomimetics, toxins (e.g., cholera toxin), tranquilizers and urinary antiinfectives.

Formulations or compositions for oral use may also be presented as hard gelatin capsules where in the active ingredient is mixed with an inert solid diluent, for example calcium carbonate, calciumphosphate or kaolin, or as soft gelatin capsules wherein the active ingredient is mixed with water or an oil medium, for example peanut oil, liquid paraffin or olive oil. Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, gum tragacanth and gum acacia; dispersing or wetting agents may be a naturally occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such a polyoxyethylene with partial esters derived from fatty acids and hexitol anhydrides, for example polyoxyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified, for example sweetening, flavoring and coloring agents, may also be present.

The terms "active compound" or active incredient" refer in the sense of the invention especially to niclosamide or derivates thereof.

The preparation of an active compound that contains a protein as an active ingredient is well understood in the art. Typically, such compounds are prepared as injectables, either as liquid solutions or suspensions; solid forms suitable for solution in, or suspension in, liquid prior to injection can also be prepared. The preparation can also be emulsified.

A "therapeutically effective amount" is preferably an amount sufficient to inhibit, partially or totally, the metastasis of a cancer.

Although the invention has been described with respect to specific embodiments and examples, it should be appreciated that other embodiments utilizing the concept of the present invention are possible without departing from the scope of the invention. The present invention is defined by the claimed elements, and any and all modifications, variations, or equivalents that fall within the true spirit and scope of the underlying principles.

EXAMPLES

Example 1: High-Throughput Screening for S100A4 Inhibitors

HCT116-S100A4p-LUC colon cancer cells stably expressing a human S100A4 promoter-driven luciferase reporter gene construct were screened with the Library of Pharmacologically Active Compounds (LOPAC; FIG. 1, A). The LOPAC Library represents a collection of 1280 well characterized small molecule inhibitors. In a primary 4-concentration screen, 34 compounds were found to inhibit S100A4 promoter-driven luciferase expression by greater than 50% compared with DMSO-treated control cells (FIG. 1, B). In parallel, cell viability was determined using the Alamar blue assay to evaluate whether some of the inhibitory effects were caused by cytotoxicity (data not shown). Of the 34 effective compounds, 11 compounds most efficiently inhibited reporter gene expression at concentrations that were non-toxic or only slightly affected cell viability. To confirm the inhibitory capacity of the selected compounds and to more accurately establish the concentration-response curves, these 11 compounds were titrated using a 20-concentration rescreen with triplicate wells at 2-fold dilutions starting with the highest test concentration of 100 µM. The concentration-response assays confirmed that niclosamide (2',5-dichloro-4'-nitrosalicylanilide) was the strongest candidate with respect to inhibition of reporter gene expression (FIG. 1, C).

Example 2: Effect of Niclosamide on S100A4 mRNA and Protein Expression

To determine an applicable niclosamide concentration, the cytotoxicity of niclosamide on HCT116 cells was analyzed. Exposure of HCT116 cells to increasing concentrations of niclosamide reduced cell viability in a concentration-dependent manner (EC50=2.2 µM; 95% CI 1.87 to 2.92 µM) (FIG. 2, A). Choosing a concentration range from 0.1 µM to 2.5 µM niclosamide endogenous S100A4 expression in HCT116 cells was analyzed and found S100A4 mRNA and protein levels to be reduced in a concentration-dependent manner (FIG. 2, B). Concentrations of more than 0.5 µM niclosamide reduced the endogenous S100A4 mRNA amount to less than 50% of the solvent-treated control (control vs niclosamide, 1 µM mean 47.4%, 95% CI 39.3% to 55.4%; P<0.01, 1.5 µM mean 39.2%, 95% CI 11.4% to 89.7%; P<0.01, 2 µM mean 39.1, 95% CI 18.3% to 59.9%, P<0.01, 2.5 µM mean 36.7%, 95% CI 18.6% to 54.8%; P<0.001). Similar effects were observed at the S100A4 protein level. No change in S100A4 expression could be detected with concentrations below 1 µM niclosamide. With respect to the optimal concentration that showed minimum cytotoxicity and maximum inhibition of S100A4 expression, 1 µM niclosamide was used for further experiments.

Next the time-dependency of niclosamide-mediated reduction of S100A4 expression was analyzed. After a single dose of niclosamide the S100A4 mRNA and protein levels in HCT116 cells were reduced to less than 50% after 18 hours and 24 hours, respectively (control vs niclosamide, 18 hours mean 47.5%, 95% CI 43.9% to 51.1%; P<0.001; 24 hours mean 47.4%, 95% CI 39.4% to 55.4%, P>0.001), but returned to the control level after 30-48 hours (FIG. 2, C). When HCT116 cells were treated daily with 1 µM niclosamide, a steady reduction of S100A4 mRNA was observed and protein levels to approximately 50% of solvent-treated control cells (control vs niclosamide, 24 hours mean 46.0%, 95% CI 38.7% to 53.3%, P<0.001; 48 hours mean 44.5%, 95% CI 32.2% to 56.8%, P<0.001; 72 hours mean 59.5%, 95% CI 50% to 69.2%, P<0.001) (FIG. 2, D).

Similar to HCT116 wild-type cells, exposure of HCT116-vector cells to niclosamide also showed approximately 50% inhibition of S100A4 expression compared with solvent-treated control cells (HCT116-vector control vs niclosamide, mean 100% vs 57.8%, mean difference 42.0%, 95% CI 31.9% to 52.1%, P<0.0001) (FIG. 2, E). In HCT116-S100A4 cells, the S100A4 mRNA level was 6-fold higher than in HCT116-vector cells because of ectopic expression of the CMV promoter-driven S100A4 cDNA construct. Consequently, S100A4 protein expression was increased in HCT116-S100A4 cells. In contrast to HCT116-vector cells, the exposure of HCT116-S100A4 to niclosamide resulted in no reduction of S100A4 mRNA (HCT116-S100A4 control vs niclosamide, mean 717.0% vs 612.3%, mean difference 104.7%, 95% CI−110.0 to 319.5, not statistically significant) and protein levels.

Example 3: Effect of Niclosamide on S100A4-Induced Cell Migration and Invasion S100A4 is a main regulator of cell motility (25). Thus, the effect of niclosamide on S100A4-induced cell migration in HCT116-vector and HCT116-S100A4 cells was analyzed. The number of migrated cells was inhibited in HCT116-vector cells in the presence of niclosamide (control vs niclosamide, mean 100.0% vs 43.0%, mean difference 57.0%, 95% CI 40.3% to 73.7%, P<0.0001) (FIG. 3, A). In contrast, migration rates of HCT116-S100A4 cells showed no reduction upon niclosamide treatment (control vs niclosamide, mean 145.0% vs 117.0%, mean difference 28%, 95% CI−7.8% to 63.9%, statistically not significant).

The invasion rates of HCT116-vector and HCT116-S100A4 cells were also determined, since S100A4 is well known to stimulate cell invasion (11). The number of invaded cells was decreased in niclosamide-treated HCT116-vector cells (control vs niclosamide, mean 100% vs 30.1%, mean difference 69.9%, 95% CI 10.9% to 128.9%, P=0.021) (FIG. 3, B). In contrast, niclosamide treatment had no effect on invasion rates of HCT116-S100A4 cells (control vs niclosamide, mean 111.4% vs 122.5%, mean difference −11.1%, 95% CI-54.9% to 32.8%, statistically not significant).

Furthermore, the effect of niclosamide on directed migration in wound healing assay was analyzed. In the absence of niclosamide HCT116-vector and HCT116-S100A4 cells completely closed the inserted wound after 4 days (FIG. 3, C). Wound closure was impaired in niclosamide-treated HCT116-vector cells. In contrast, HCT116-S100A4 cells were able to migrate into the wound and close the gap despite the presence of niclosamide. In summary, exposure to niclosamide restricted cell motility and invasiveness. This effect was specific to S100A4, since ectopic overexpression of S100A4 overcame the niclosamide-mediated inhibition of cell motility.

Example 4: Effect of Niclosamide on Anchorage-Dependent and -Independent Cell Growth The anchorage-dependent cell proliferation in the presence or absence of niclosamide and in dependency of the S100A4 expression level was measured. Exposure of HCT116-vector cells and HCT116-S100A4 cells to niclosamide resulted in a reduction of cell proliferation in both cell lines independent on the expression level of S100A4 (FIG. 3, D). Anchorage-independent growth was analyzed by colony formation assay. Solvent-treated HCT116-vector and HCT116-S100A4 cells were both able to form large colonies within seven days (FIG. 3, E). However, treatment with niclosamide clearly reduced the colony size of HCT116-vector and HCT116-S100A4 cells. Further, the number of HCT116-vector and HCT116-S100A4 cell colonies was severely reduced (HCT116-vector control vs niclosamide, mean 100% vs 6.8%, mean difference 93.2%, 95% CI 84.2 to 102.2%, P<0.0001; HCT116-S100A4 control vs niclosamide, mean 105.8% vs 5.0%, mean difference 100.7%, 95% CI 89.5% to 111.9%, P<0.0001) (FIG. 3, F). In summary, inhibition of cell proliferation and colony formation by niclosamide was independent on the level of endogenous or ectopic S100A4 expression.

Example 5: Effect of Niclosamide on S100A4-Induced Motility and Proliferation of Human Colon Cancer Cells Next the effects of niclosamide on S100A4 expression in the colon cancer cell lines SW620, LS174T, SW480, and DLD-1 were analyzed. Niclosamide treatment reduced the S100A4 mRNA level in SW620, LS174T and SW480 cells to less than 30% of the respective solvent-treated control (SW620 control vs niclosamide, mean 100.0% vs 31.2%, mean difference 68.8%, 95% CI 49.1% to 88.5%, P<0.0001; LS174T control vs niclosamide, mean 65.5% vs 13.5%, mean difference 51.9%, 95% CI 38.3% to 65.6%, P<0.0001, SW480 control vs niclosamide, mean 41.0% vs 6.0%, mean difference 35.0%, 95% CI, 27.1% to 42.9%, P<0.0001) (FIG. 4, A). In DLD-1 cells the S100A4 mRNA was barely detectable and remained unchanged under niclosamide treatment. Further, niclosamide reduced the S100A4 protein expression in SW620, LS174T and SW480 cells, whereas no S100A4 protein was detected in solvent and niclosamide-treated DLD-1 cells.

Niclosamide treatment reduced the cell migration rate of SW620, LS174T, and SW480 cells to less than 50% of the respective solvent-treated control (SW620 control vs niclosamide, mean 100.0% vs 47.9%, mean difference 52.1%, 95% CI 25.4% to 78.9%, P=0.0005; LS174T control vs niclosamide, mean 68.2% vs 26.8%, mean difference 41.3%, 95% CI 16.3% to 66.3%, P=0.0024; SW480 control vs niclosamide, mean 21.7% vs 10.6% mean difference 11.1%, 95% CI 1.2% to 2.1%, P=0.0297). Solvent-treated DLD-1 cells presented the lowest migration rate, which was not further affected by niclosamide treatment (FIG. 4, B). Similarly, cell invasion of SW620, LS174T and SW480 cells was inhibited to less than 30% of the respective solvent-treated control (SW620 control vs niclosamide, mean 100.0% vs 25.1%, mean difference 74.9%, 95% CI 48.4% to 101.4%, P<0.0001; LS174T control vs niclosamide, mean 63.2% vs 23.6%, mean difference 39.5%, 95% CI 8.7% to 70.4%, P=0.013; SW480 control vs niclosamide, mean 47.7% vs 12.8%, mean difference 34.9%, 95% CI 12.3% to 57.5%, P=0.0031) (FIG. 4, C). The low invasion rate of solvent-treated DLD-1 cells was not affected by niclosamide treatment. Directed migration of SW620, LS174T, SW480 and DLD-1 cells, as measured in the wound healing assay, was impaired upon niclosamide treatment compared with the respective solvent-treated control (FIG. 4, D). Consistent with their lower migration rate, solvent-treated DLD-1 cells did not close the wound until day 4.

Anchorage-dependent cell proliferation of all four cell lines was inhibited under niclosamide treatment (FIG. 4, E). Moreover, anchorage-independent growth was impaired when SW620, LS174T, SW480 and DLD-1 cells were exposed to niclosamide, resulting in clearly smaller cell colonies (FIG. 4, F). Niclosamide treatment reduced the number of colonies to less than 50% in all four colon cancer cells lines (SW620 control vs niclosamide, mean 100.0% vs 3.6%, mean difference 96.4%, 95% CI 78.0% to 114.8%, P<0.0001; LS174T control vs niclosamide, mean 90.6% vs 15.9%, mean difference 74.6%, 95% CI 58.3% to 91.0%, P<0.0001; SW480 control vs niclosamide, mean 68.1% vs 4.3%, mean difference 63.8%, 95% CI 52.2% to 75.4%, P<0.0001; DLD-1 control vs niclosamide, mean 82.6% vs 10.1%, mean difference 72.5%, 95% CI 52.5% to 92.4%, P<0.0001) (FIG. 4, G). In summary, in colon cancer cells with increased S100A4 expression levels, niclosamide inhibited cell-migration and invasion. Cell proliferation was inhibited independently of the S100A4 expression level.

Example 6: Efficiency of Niclosamide Derivatives on S100A4 Expression and Cell Migration The effect of structural changes in the niclosamide molecule on its ability to restrict S100A4 expression (FIG. 5, A) was analyzed. To compare the efficiency of niclosamide and its derivates to inhibit S100A4 expression all compounds were applied at the treatment conditions defined for niclosamide. In contrast to the observed effects of niclosamide, no reduction of S100A4 mRNA and protein levels were detected with any of the six niclosamide derivatives (FIG. 5, B). However, the further derivatives did show a significant decrease of migration rates upon analysis of cell migration (FIG. 5, C). In summary, none of the niclosamide derivatives topped the effect of niclosamide to restrain S100A4 expression and S100A4-induced cell motility. However, the further derivatives maintained an effect against cell motility and showed under some conditions more effective results, for example in speed of effect in various models in addition to potential improvements in solubility and potentially pharmaceutical formulation. It was concluded that these changes in the structure of niclosamide result in a loss of its efficiency towards S100A4 expression inhibition but provide potentially other beneficial effects.

Example 7: Effect of Niclosamide on Constitutively Active WNT Signaling

As published earlier HCT116 cells are heterozygous for mutated CTNNB1 resulting in constitutively active WNT signaling and S100A4 expression (4). Applying the LEF/TCF transcription factor reporter (TOP/FOPflash) assay the WNT/CTNNB1 pathway activity in niclosamide-treated HCT116 cells was analyzed, as well as in its knockout derivative cells HAB-68mut and HAB-92 wt which only bear the mutated or wild-type allele of CTNNB1, respectively. In the absence of niclosamide WNT pathway activity was 1.3-fold increased in HAB-68mut cells and 2.9-fold decreased in HAB-92 wt cells compared with HCT116 cells. Exposure to niclosamide resulted in a decrease of WNT pathway activity in HCT116, HAB-68mut and HAB-92 wt cells (HCT116 control vs niclosamide, mean 1.00 vs 0.39, mean difference 0.61, 95% CI 0.41 to 0.81, P<0.0001; HAB-68mut control vs niclosamide, mean 1.39 vs 0.50, mean difference 0.90, 95% CI 0.64 to 1.16, P<0.0001; HAB-92 wt control vs niclosamide, mean 0.36 vs 0.21, mean difference 0.15, 95% CI 0.05 to 0.25, P=0077) (FIG. 6, A). Niclosamide treatment also resulted in a decrease of S100A4 mRNA and protein expression (HCT116 control vs niclosamide, mean 1.00 vs 0.46, mean difference 0.54, 95% CI 0.43 to 0.65, P<0.0001; HAB-68mut control vs niclosamide, mean 1.17 vs 0.62, mean difference 0.55, 95% CI 0.41 to 0.69, P<0.0001; HAB-92 wt control vs niclosamide, mean 0.03 vs 0.01, mean difference 0.02, 95% CI−0.001 to 0.047, statistically not significant) (FIG. 6, B). Consistently, migration rates of HCT116 and HAB-68mut cells were reduced to the level of HAB-92 wt cells upon niclosamide treatment (HCT116 control vs niclosamide, mean 1.00 vs 0.45, mean difference 0.54, 95% CI 0.22 to 0.87, P=0.0015; HAB-68mut control vs niclosamide, mean 1.30 vs 0.39, mean difference 0.91, 95% CI 0.62 to 1.20, P<0.0001; HAB-92 wt control vs niclosamide, mean 0.36 vs 0.32, mean difference 0.04, 95% CI−0.08 to 0.16, statistically not significant) (FIG. 6, C). In summary, niclosamide inhibits WNT signaling-dependent target gene transcription despite a constitutively active WNT/CTNNB1 pathway.

Example 8: Mode of Action of Niclosamide on the WNT/CTNNB1 Pathway

Active WNT signaling is highly dependent on nuclear CTNNB1. Accordingly, the amount of nuclear CTNNB1 under increasing concentrations of niclosamide was analyzed. Exposure of HCT116 cells to increasing concentrations of niclosamide for 18 hours did not change the protein level of nuclear CTNNB1 (FIG. 6, D). However, a reduction in WNT/CTNNB1 signaling and in S100A4 gene expression was not observed. This led to the hypothesis that niclosamide might act within the nucleus to inhibit the formation of the CTNNB1/TCF transcription activating complex. This hypothesis was tested by EMSA, applying biotinylated oligonucleotides which encompassed the TCF-binding site of the S100A4 promoter. Oligonucleotide shifts caused by binding of TCF and CTNNB1/TCF were detected in the absence of niclosamide (FIG. 6, E), which is consistent with previous findings (4). The presence of CTNNB1 within the complex was verified by complexation with monoclonal anti-CTNNB1 leading to a supershift. Exposure of HCT116 cells to increasing concentrations of niclosamide interrupted the CTNNB1/TCF/oligo complex in a concentration-dependent manner. No supershift could be detected in nuclear extracts from 1 µM niclosamide-treated cells. Consistent with these results, the ChIP assay showed that no S100A4 promoter sequence could be PCR amplified after CTNNB1-immunoprecipitation from niclosamide-treated cell extracts, but PCR product was detected from solvent-treated cell extracts (FIG. 6, F). The latter was already observed by Stein et al (4). No PCR product could be detected when control immunoglobulin G was used for precipitation or when FOS promoter sequence was PCR amplified. In summary, it was concluded that niclosamide treatment inhibits CTNNB1/TCF complexation and thereby inhibits WNT/CTNNB1 target gene transcription.

Example 9: Effect of Niclosamide on Metastasis Formation In Vivo

Next, the effect of niclosamide on metastasis formation in xenograft mice by non-invasive in vivo luminescence imaging was monitored. On day 8 after intrasplenic transplantation of HCT116-CMVp-LUC cells, stably expressing firefly luciferase, a visible spleen tumor has formed in solvent-treated control mice and in 20 mg per kg niclosamide-treated mice (FIG. 7, A). Lateral imaging showed that the spleen tumor signal increased in solvent and niclosamide-treated mice until it reached a maximum on day 24. Differences in signal localization were found by ventral imaging. In control mice a liver metastasis signal could be detected which was confirmed by in situ imaging and isolation of liver and spleen. No or only tiny liver metastasis signals could be detected in niclosamide-treated mice.

Niclosamide was able to inhibit S100A4 expression in vivo, since S100A4 mRNA levels were reduced in niclosamide-treated mice (control vs 2×15 mg per kg, mean 100.0% vs 58.4%, mean difference 41.7%, 95% CI 21.6% to 61.8%, P<0.001; control vs 20 mg per kg, mean 100.0% vs 67.2%, mean difference 32.9%, 95% CI 14.1% to 51.7%, P<0.001) (FIG. 7, B). Liver metastasis score was diminished in niclosamide-treated mice compared with solvent-treated mice (control mean 100.0%, 95% CI−15.4% to 215.4%; 2×15 mg per kg mean 36.1%, 95% CI 12.4% to 59.8%; 20 mg per kg mean 37.9%, 95% CI 22.6% to 53.1%) (FIG. 7, C). In summary, it was concluded that niclosamide treatment inhibits S100A4-induced metastasis formation in vivo.

Example 10: Long-Term Effect of Niclosamide Treatment In Vitro and In Vivo

Next the effect on S100A4-mediated metastasis formation when niclosamide treatment is discontinued was investigated. To approach this, HCT116 cells were traited daily with niclosamide for three consecutive days. On day 4 niclosamide was removed. The S100A4 expression in these cells remained repressed to about 50% of the respective solvent-treated control for 24, 48 and 72 hours after discontinuation of niclosamide exposure (control vs niclosamide 24 hours post-treatment, mean 101.9% vs 58.0%, mean difference 43.9%, 95% CI 31.0% to 56.8%, P=0.0002; control vs niclosamide 48 hours post-treatment, mean 98.1% vs 44.4%, mean difference 53.7%, 95% CI 33.2% to 74.1%, P=0.0011; control vs niclosamide 72 hours post-treatment, mean 100.0% vs 57.9%, mean difference 42.1%, 95% CI 16.6% to 67.6%, P=0.0193) (FIG. 8, A). Further, S100A4 protein was clearly reduced for three days following the discontinuation of niclosamide treatment. Cell migration rates in these cells remained repressed to less than 30% of the respective solvent-treated control for up to three days after removal of niclosamide (control vs niclosamide 24 hours post-treatment, mean 100.0% vs 18.7%, mean difference 81.3%, 95% CI 40.7% to 122.0%; P=0.0004; control vs niclosamide 48 hours post-treatment, mean 100.0% vs 12.2%, mean difference 87.8%, 95% CI 54.9% to 120.7%, P<0.0001; control vs niclosamide 72 hours post-treatment, mean 108.8% vs 10.4%, mean difference 98.4%, 95% CI 41.5% to 155.4%, P=0017) (FIG. 8, B).

Anchorage-dependent proliferation of niclosamide-treated HCT116 cells was inhibited compared with the solvent-treated control (FIG. 8, C). After five days, solvent-treated control cells reached the maximum. Removal of niclosamide on day 5 did not reverse the inhibition of cell proliferation for the following five days when compared with continuously niclosamide-treated cells.

Furthermore, the metastasis formation in vivo was investigated under continuous and discontinuous niclosamide treatment. The overall survival of niclosamide-treated mice was prolonged compared with solvent-treated mice (control vs discontinuous treatment, median survival 24 days vs 46.5 days, ratio 0.52, 95% CI 0.19 to 0.84, P=0.0012; control vs continuous treatment, median survival 24 days vs 43 days; ratio 0.56, 95% CI 0.24 to 0.88, P=0.0012) (FIG. 8, D). Furthermore, no difference in overall survival was observed in mice in which the treatment was discontinued after 24 days compared with mice under continuous niclosamide treatment.

On the individual end-point of each mouse, the liver and spleen were removed and applied to in vivo luminescence imaging. All animals developed a spleen tumor. However, tumor growth in niclosamide-treated mice, either continuously or discontinuously, was clearly delayed compared with solvent-treated mice (FIG. 8, E). The size of liver metastases in continuously and discontinuously niclosamide-treated mice was clearly reduced compared with solvent-treated animals. In discontinuously niclosamide-treated mice liver metastases were slightly larger than in continuously niclosamide-treated mice. However, the luminescence signals from liver metastases of control animals were stronger on day 29 than the signal of liver metastases of continuously or discontinuously niclosamide-treated animals on day 50 indicating a long-term inhibition of metastasis formation by niclosamide.

Quantification of the S100A4 mRNA level in the spleen tumor tissue revealed that in niclosamide-treated mice the S100A4 mRNA was repressed (control vs discontinous treatment, mean 100.0% vs 60%, mean difference 40.0%, 95% CI 3.9% to 50.1%, P<0.001; control vs continuous treatment, mean 100.0% vs 73%, mean difference 27%, 95% CI 15.8% to 64.2%, P<0.05) (FIG. 8, F). Moreover, no statistical significant difference in the S100A4 expression level could be detected in mice with continuous versus discontinuous niclosamide treatment. Consistent with this result, liver metastasis was reduced in niclosamide-treated mice compared with control mice (control vs discontinuous treatment, mean 100.0% vs 34.9%, mean difference 65.1%, 95% CI 18.4% to 111.9%, P<0.01; control vs continuous treatment, mean 100.0% vs 10.9%, mean difference 89.1%, 95% CI 45.3% to 133.0%, P<0.001) (FIG. 8, G). Moreover, no statistical significant difference was observed in mice with discontinued niclosamide treatment compared with mice with continuous niclosamide treatment. In summary, even when niclosamide is not continuously given, S100A4 expression and metastases formation were severely inhibited leading to a prolonged overall survival.

The use of mouse models in the above provided examples is not limiting for the present invention, which is intended for application in human subjects. The mouse model represents a standard accepted model for human application and provides reliable support for application in mammals, including preferably humans.

Materials and Methods Used in the Examples

Cell Lines and Cell Culture

Human colon cancer cell lines SW620, LS174T, SW480, DLD-1 and HCT116 were all grown in RPMI-1640 medium (PAA Laboratories, Pasching, Austria) supplemented with 10% fetal bovine serum (FBS; Invitrogen). HCT116 cells were previously described to be heterozygous for the deletion mutation of codon 45 in one of the two CTNNB1 alleles resulting in the loss of serine 45 which is the initial phosphorylation site in CTNNB1 protein needed for proteasomal degradation. Homologous recombination was used to delete the wild-type CTNNB1 allele resulting in the HCT116 derivative cell clone HAB-68mut or to delete the mutated CTNNB1 allele resulting in the HCT116 derivative cell clone HAB-92 wt (20). Both cell clones were kindly provided by Dr Todd Waldman (Georgetown University, Washington, District of Columbia). All cells were expanded briefly in culture and cryopreserved in multiple replicate vials. These cell banks were tested by PCR and culture methods and found to be free of mycoplasma. To authenticate the HAB-68mut and HAB-92 wt cell lines as HCT116 derivatives, short tandem repeat (STR) genotyping was performed in August, 2010 using the ABI Identifier Kit (Applied Biosystems). The STR genotypes were consistent with published genotypes for HCT116 (20). All cells were kept in a humidified incubator at 37° C. and 5% CO2.

Monoclonal and Polyclonal Antibodies

The monoclonal mouse anti-human-CTNNB1 antibody and the monoclonal mouse anti-human tubulin-β1 (TUBB1) antibody were both purchased from BD Biosciences, Heidelberg, Germany. The monoclonal mouse anti-human-proliferating cell nuclear antigen (PCNA) antibody was purchased from Cell Signaling Technologies, Danvers, Mass. The polyclonal rabbit anti-human-S100A4 antibody was purchased from Dako, Glostrup, Denmark. The polyclonal goat anti-human-glyceraldehyde-3-phosphate dehydrogenase (GAPDH) antibody and the horseradish peroxidase (HRP)-conjugated anti-goat antibody were purchased from Santa Cruz Biotechnology, Santa Cruz, Calif. HRP-conjugated anti-rabbit was purchased from Promega Madison, Wis. HRP-conjugated anti-mouse IgG and anti-mouse IgM were purchased from Invitrogen.

Stable Transfections of HCT116 Cells

We PCR amplified the S100A4 promoter sequence (−1487 bp upstream sequence to S100A4 transcription start site) from a vector kindly provided by Dr David Allard (Peninsula Medical School, Universities of Exeter and Plymouth, Exeter, UK) and cloned it into the pGL1.4 vector (Invitrogen) to gain the firefly luciferase (LUC) reporter gene under the control of S100A4 promoter with neomycin resistance cassette (21). This construct was transfected into HCT116 cells to gain HCT116-S100A4p-LUC cells. We cloned the S100A4 cDNA sequence from a vector kindly provided by Dr Claus Heizmann (22) (University of Zurich, Zurich, Switzerland) into the pcDNA3.1 vector with a puromycin resistance cassette. This construct was transfected into HCT116 cells to gain HCT116-S100A4 cells or the empty vector to gain HCT116-vector cells. We cloned the LUC reporter gene under the control of CMV promoter and transfected HCT116 cells to gain HCT116-CMVp-LUC cells. All cloned constructs were performed in our lab and sequenced for correct in-frame orientation. All transfections were performed with Metafectene (Biontex Laboratories, Munich, Germany), according to the manufacturer's instructions. To gain stable transgene expressing cells 1 mg per mL neomycin (PAA Laboratories) or 1 μg per mL puromycin (Invitrogen, Carlsbad, Calif.) were used for selection.

High-Throughput Screening

For high-throughput screening 2.5×103 cells per well of HCT116-S100A4p-LUC cells were seeded into white opaque 384-well plates (Perkin Elmer, Waltham, Mass.) using the BIOMEK 2000 automatic pipetting system (Beckman Coulter, Brea, Calif.). All 1280 compounds of the Library of Pharmacologically Active Compounds (LOPAC 1280; obtained from Sigma-Aldrich, St Louis, Mo.) were dissolved initially in dimethylsulfoxide (DMSO) and then diluted in RPMI-1640 culture medium. Samples of test compounds were then added to assay plates containing cells which were treated for 24 hours with each compound at concentrations of 0.1 μM, 1 μM, 10 μM and 100 μM (single well per concentration). Following compound treatment, luciferase expression was determined using Britelite reagent (Perkin Elmer) in a Wallac Victor reader (Perkin Elmer). In parallel, cytotoxicity of the compounds was measured in clear polystyrene 384-well plates (Costar) by Alamar blue cytotoxicity assay (Sigma-Aldrich). Following 24 hours compound treatment, Alamar blue dissolved in serum-free RPMI-1640, was added to each well and incubation continued for four hours. Plates were then read on a Wallac Victor reader at an excitation wavelength of 530 nm and emission wavelength of 590 nm. For both luminescence and Alamar blue fluorescence data, eight vehicle control wells were averaged and test compound results (single well) expressed as percent of control. The concentrations effective in reducing luciferase activity or Alamar blue fluorescence by 50% were derived from concentration-response curves by linear interpolation. The Alamar blue vs luciferase ratio representing the toxicity vs activity ratio (2.0) was used to triage the screening data. In addition, as a selectivity screen, inhibitory compounds were also analyzed based on their capacity to inhibit HIF-1α-driven or constitutive luciferase reporter expression in U251 glioma cell lines used in a previous high-throughput screen of LOPAC (23). Compounds showing the best evidence for selective reporter inhibition not due to toxicity were then subjected to detailed concentration-response testing in both assays using duplicate wells per concentration and 20 two-fold dilutions from a top concentration of 100 W.

Drugs and Treatments

Niclosamide (2',5-dichloro-4'-nitrosalicylanilide) was obtained from Sigma-Aldrich (St Louis, Mo.). Niclosamide derivatives were obtained from the Drug Synthesis and Chemistry Branch, Developmental Therapeutics Program, NCI, Bethesda, Md. All drugs were solubilized in DMSO for in vitro application. In vivo niclosamide was administered as suspension in 10% cremophore EL (BASF, Ludwigshafen, Germany) and 0.9% NaCl solution.

Quantitative Reverse Transcription-Polymerase Chain Reaction (qRT-PCR)

Total RNA was isolated from 4×105 cells plated in a 6-well-plates 24 hour before cells were lyzed with Trizol Reagent (Invitrogen). RNA was extracted with Trizol RNA extraction reagent (Invitrogen) according to the manufacturer's instructions. Quantification of the RNA concentration was performed with Nanodrop (Peqlab) and 50 ng total RNA was reverse transcribed with random hexamers in 10 mM MgCl2; 1× RT-buffer, 250 µM pooled dNTPs, 1 U per µL RNAse inhibitor and 2.5 U per µL MuLV reverse transcriptase (all Applied Biosystems). Reaction occurred at 42° C. for 15 minutes, 99° C. for 5 minutes and subsequent cooling at 5° C. for 5 minutes. The cDNA product was amplified in a total volume of 10 µL in 96-well-plates in the LightCycler 480 (Roche) using the following conditions: 95° C., 10 minutes, followed by 45 cycles of 95° C. for 10 seconds, 61° C. for 30 seconds and 72° C. for 4 seconds. For S100A4 cDNA quantification the following primer and probes were used: forward primer 5'-CTCAGCGCTTCTTCTTTC-3', reverse primer 5'-GGGTCAGCAGCTCCTTTA-3', fluorescein isothiocyanate probe 5'-TGTGATGGTGTCCACCTTCCACAAGT-3', LCRed640-probe 5'-TCGGGCAAAGAGGGTGACAAGT-3'. For cDNA quantification of the housekeeping gene glucose-6-phosphate dehydrogenase (G6PD) the hG6PDH Roche Kit (Roche Diagnostics, Mannheim, Germany) was used according to manufacturers instructions. Data analysis was performed with LightCycler® 480 Software release 1.5.0 SP3. For each qRT-PCR reaction a mean of the duplicate was calculated. Each mean value of the expressed gene was normalized to the respective mean amount of the G6PD cDNA.

Immunoblot

For total protein extraction cells were lysed with RIPA buffer (50 mM Tris-HCl, 150 mM NaCl, 1% Nonidet P-40, supplemented with complete protease inhibitor tablets; Roche) for 30 minutes on ice. For isolation of the nuclear protein fraction, the NE-PER Nuclear and Cytoplasmic Extraction Kit (Pierce) was used according to the manufacturer's instructions. Protein concentration was quantified with Bicinchoninic Acid (BCA) Protein Assay Reagent (Pierce) according to manufacturer's instructions and lysates of equal protein concentration were separated with SDS-PAGE and transferred to Hybond C Extra nitrocellulose membrane (Amersham Biosciences). Membranes were incubated in blocking solution containing 5% nonfat dry milk and 1% bovine serum albumin (BSA) for 1 hour at room temperature. Membranes were incubated overnight at 4° C. with rabbit anti-human-S100A4 antibody (dilution, 1:1500), mouse anti-human-CTNNB1 antibody (dilution, 1:1000), mouse anti-human TUBB1 antibody (dilution, 1:1000), goat anti-human GAPDH antibody (dilution, 1:500) or mouse anti-human PCNA antibody (dilution, 1:1000) followed by incubation for 1 hour at room temperature with HRP-conjugated anti-goat (dilution, 1:10000), anti-rabbit (dilution, 1:10000), anti-mouse IgG (dilution, 1:10000) or anti-mouse IgM (dilution, 1:10000) antibody. Antibody-protein-complexes were visualized with electro-chemical-luminescence (ECL) reagent (100 mM Tris-HCl, 0.025% w/v luminol, 0.011% w/v para-hydroxycoumaric acid, 10% v/v dimethylsulfoxide, 0.004% v/v H2O2, pH 8.6) and subsequent exposure to CL-XPosure™ Films (Pierce) for 1 second to 20 minutes. Immunoblotting for GAPDH and PCNA served as protein loading control. Immunoblotting for β-tubulin was used to control that nuclear extracts were free from cytoplasmatic protein. All experiments were performed at least three independent times.

Boyden Chamber Transwell Migration and Invasion Assay

HCT116, SW620, LS174T, SW480 and DLD-1 cells were used in cell migration and invasion analysis performed with Boyden chamber assay. 400 µL containing 2.5×105 cells were seeded into each transwell chamber with filter membranes of 12.0 µm pore size (Millipore, Schwalbach, Germany). For invasion filter membranes were coated with 50 µL Matrigel (diluted 1:3 in RPMI-1640; BD Biosciences) 10 minutes before cells were seeded. Fresh medium (600 µL) were added to the bottom chamber and cells were allowed to attach to the insets for 15 hours. Both chambers were treated with 1 µM niclosamide or the respective amount of DMSO and incubated at 37° C. and 5% CO2 in a humidified incubator for 24 hours. Afterwards insets were removed and cells that had migrated through the membrane to the lower chamber were trypsinized and counted in a Neubauer chamber (LO-Laboroptik, Bad Homburg, Germany). Each well was counted ten times. Each migration or invasion experiment was performed in duplicate. The average number of migrated or invaded cells was determined for at least three independent experiments.

Wound Healing Assay

For wound healing assay HCT116, SW620, LS174T, SW480 and DLD-1 cells were grown to form 60% confluent monolayers of cells in which a wound of about 300 µm width was inflicted with a sterile pipette tip. The medium was exchanged to remove non-adherent cells and the wounded monolayer was treated with 1 µM niclosamide or the respective amount of DMSO every 24 hours for 4 consecutive days. The progress of wound closure was monitored with microphotographs of 10× magnification taken with the Leica DM IL light microscope (Leica Microsystems) on day 0 and day 4. The wound healing experiment was performed three independent times.

Anchorage-Dependent Cell Proliferation

For cell proliferation determination of HCT116, SW620, LS174T, SW480 and DLD-1 cells $2\times10^3$ cells were seeded in 96-well-plates (for each day one plate) and were given 24 hours to attach to the bottom of the well. Cells were from then on treated daily with 1 µM niclosamide or the respective amount of DMSO. For determination of viable cells 3-(4,5-dimethyl-2-thiazol)-2,5-diphenyl-2H-tetrazolium bromide (MTT; Sigma) was added to a final concentration of 0.5 mg per mL and incubated for 3 hours at 37° C. and 5% $CO_2$ in a humidified incubator. MTT was reduced to purple formazan crystals by the mitochondria of living cells and the increase in metabolized MTT reflected the increase in the number of cells. Crystallized MTT was resolved by 10% SDS in 10 mM HCl and the absorption was measured at 560 nm. MTT measurements were performed daily for 5 consecutive days. The average MTT metabolisation was determined of two independent experiments each performed in triplicate.

Colony Formation Assay

Analysis of anchorage-independent cell proliferation was achieved by soft agar colony formation assay. A bottom layer containing 0.5% w/v agarose, RPMI-1640 medium, 10% FBS and 1 µM niclosamide or the respective amount of DMSO was added to a 6 cm Ø dish and incubated at room temperature under sterile conditions for 10 minutes. Onto the solidified bottom layer a top layer was added containing $8\times10^3$ cells, 0.33% w/v agarose, RPMI-1640 medium, 10% FBS and 1 µM niclosamide or the respective amount of DMSO. Cells were seeded as single cells into the soft agar and incubated in a humidified incubator at 37° C. and 5% $CO_2$ for 7 days. Colony formation was visualized by 10× magnification for an overview and 40× magnification for single colonies in the Leica DM IL light microscope (Leica Microsystems). Colony quantification was achieved by counting cell colonies of more than 4 cells in 10 squares of 1 µm². Colony formation experiments were repeated twice, each in triplicates.

WNT/CTNNB1 Pathway Activity Reporter Assay

The lymphoid enhancer-binding factor 1 (LEF)/transcription factor (TCF) activity reporter assay, also known as TOP/FOPflash assay (Promega, Madison, Wis.) was previously used to analyze the WNT/CTNNB1 pathway activity in human colon cancer cells (24). It comprises the TOPflash plasmid which contains a hexameric repetition of the LEF/TCF-binding element upstream of a thymidine kinase (TK) promoter and firefly luciferase as reporter gene. The FOPflash plasmid comprised the exact sequence of the TOPflash plasmid, but with point mutated LEF/TCF-binding sites. In the assay, $8\times10^4$ HCT116 cells were plated in 24-well-plates and were given 15 hours to attach to the bottom of the well. Cells were transfected with TOPflash or FOPflash plasmids using Metafecten according to the manufacturer's instruction 24 hours before they were treated with 1 µM niclosamide or the respective amount of DMSO for another 24 hours. Luciferase activity as read out for LEF/TCF activity and thus WNT/CTNNB1 pathway activity was measured by the Steady Glow™ Luciferase Assay System (Promega) according to the manufacturer's instructions in the luminescence reader SpectraFluor Plus (Tecan) with 1500 milliseconds exposure time and a gain of 150. TOPflash reporter gene expression (representing the WNT pathway activity) was normalized to FOPflash reporter gene expression (representing basal reporter gene expression and transfection efficiency). The average of three independent experiments is given here, whereas each experiment was performed in duplicate.

Electrophoretic Mobility Shift Assay

Electrophoretic mobility shift assay (EMSA) was performed as described earlier (4). $5\times10^6$ HCT116 cells were plated into a 10 cm culture dish and were given 15 hour to attach to the bottom of the dish. Cells were treated with 0.1, 0.3, 0.6 or 1 µM niclosamide or the respective amount of DMSO for 24 hours. For each condition 5 µg nuclear extracted protein was incubated 30 minutes at room temperature with 0.05% w/v poly dI•dC, 0.5 mM Tris, 0.05 mM EDTA, 2.5% v/v glycerol, 0.2% v/v NP-40, 5 mM MgCl2 and double-stranded biotinylated oligonucleotides (sense 5'-CCGGGCATGGGGATCCC-CACCCCAGTTTTTGTTTCTGAATCTTTATTTTTT-TAAGAGACA-3', antisense 3'-GGCCCGTACCCCTAGGGGTGGGGT-CAAAAACAAAGACTTAGAAATAAAAAAATTCTCTG T-5') encompassing the TCF-binding site of the S100A4 promoter. For supershift 1.25 µg monoclonal CTNNB1 antibody (BD Biosciences) was added. Electrophoretic separation of the protein-oligonucleotide-complexes was performed in pre-cast Novex 6% TBE gels (Invitrogen) and in TBE buffer (45 mM Tris, 45 mM boric acid, 1 mM EDTA, pH 8.3) for 60 minutes at 100 V. Capillary transfer of the protein-oligonucleotide-complexes to the Hybond™-N nylon membrane (Amersham Biosciences) occurred in 20×SSC buffer (3 M NaCl, 300 mM Na3C6H5O7, pH 7) overnight. Cross-linkage of transferred DNA to the membrane occurred at 250 mJ per cm² for 1 minute in the FL-20-M FluoLink Crosslinker (Bachofer). Visualization of biotin-labeled DNA was performed with LightShift Chemiluminescent EMSA Kit (Pierce) according to manufacturer's instructions. One representative of at least two independent experiments is shown here.

Chromatin Immunoprecipitation

Chromatin immunoprecipitation (ChIP) was described earlier to determine the binding of CTNNB1 to the S100A4 promoter (4). For the preparation of cell lysates $1\times10^6$ HCT116 cells were plated in 10 cm Ø dish 15 hours before cells were treated with 1 µM niclosamide or the respective amount of DMSO for 24 hours. Cells were incubated with 1% formaldehyde for 10 minutes at room temperature to assure reversible cross-linking of proteins and DNA. Cells were washed twice with ice-cold PBS and lyzed with lysis buffer A (1% SDS, 10 mM EDTA, 50 mM Tris-HCl, pH8) for 10 minutes on ice. Cell lysates were sonicated for 20 pulses at 40% output and centrifuged at 10000 rpm for 10 minutes. Supernatant was transferred to a new tube and one third of the diluted supernatant was stored at −20° C. and served in the end as input control. For immunoprecipitation the diluted supernatant was incubated with 5 µg monoclonal CTNNB1 antibody or 5 µg control IgG (both BD Biosciences) overnight at 4° C. Protein G beads (Invitrogen) were added and incubated for 2 hours at 4° C. Non-bound protein was washed away twice with wash buffer A (10 mM Tris, 0.1% SDS, 0.1% Na-deoxycholate, 1% Triton X-100, 1 mM EDTA, 0.5 mM EGTA, 140 mM NaCl, pH 8), once with wash buffer B (wash buffer A, 6% w/v NaCl) and twice with TE buffer (20 mM Tris, 1 mM EDTA, pH 8). Elution of the protein-DNA-complex from the beads occurred by incubation with 1.5% w/v SDS solution for 15 minutes at room temperature followed by centrifugation at 3000 rpm for 1 minute. To assure complete elution a second elution step was performed by incubation of the beads in 0.5% SDS solution for 15 minutes at room temperature followed by centrifugation at 3000 rpm for 1 minute. Cross linking was reversed at 68° C. for 4 hours and residual protein was digested by proteinase K (Fermentas, St. Leon-Rot, Germany) at 55° C. for 2 hours. DNA was purified by precipitation and PCR amplification of the S100A4 promoter TCF-binding site (forward primer 5'-TGTTCCCCTCCAGATCCC-3'; reverse primer 5'-GGCTATGCTCAAGCCACTG-3') was performed. PCR amplification of the non-CTNNB1 regulated FBJ murine osteosarcoma viral oncogene homolog (FOS) promoter sequence (forward primer 5'-CCTTAATATTCC-CACACATGGC-3', reverse primer 5'-CTGCGTTTG-GAAGCAGAAAGT-3') served as a control. The expected amplicons for S100A4 and FOS were 167- or 149 bp in size, respectively. ChIP was performed in two independent experiments.

In Vivo Luminescence Imaging of Metastasis Formation

All experiments were performed in accordance with the UKCCCR guidelines and approved by the responsible local authorities (State Office of Health and Social Affairs, Berlin, Germany). HCT116-CMVp-LUC cells (3×106 cells per mouse, resuspended in 50 μL PBS) were intrasplenically transplanted into 6-week-old female nonobese diabetic-severe combined immunodeficiency (NOD-SCID) mice. Mice were randomly assigned to 3 groups and reatment of mice started 24 hours after cell transplantation. Mice of the control group (n=9) were treated with daily doses of solvent. Mice of the second group (n=9) were daily treated intraperitoneally with 20 mg per kg niclosamide. Mice of the third group (n=9) were treated intraperitoneally with two doses of 15 mg per kg niclosamide per day. The experimental endpoint was reached when mice appeared moribund and/or the spleen tumor was palpable. This was the case with the majority of control mice on day 24. For long-term in vivo experiments mice randomly assigned to 3 groups. Mice of the control group (n=6) were treated intraperitoneally with daily doses of solvent. Mice of the second group (n=6) were daily treated intraperitoneally with 20 mg per kg niclosamide. Mice of the third group (n=6) were daily treated intraperitoneally for 24 days with 20 mg per kg niclosamide and for the residual days with solvent. Mice were killed by cervical dislocation when tumor reached the maximum in accordance with the local authorities.

Spleen (as the transplantation site) and liver (as a metastasis target organ) were removed. The amount of S100A4 mRNA in the tumor was determined by Trizol RNA isolation of tumor cryosections and quantitative real-time RT-PCR. The level of metastasis was evaluated by scoring. For each liver, a score was calculated as the sum of the volumes of the individual metastases. For each metastasis the formula [width2]×length was applied.

For in vivo luminescence imaging mice were anesthetized with 35 mg per kg Hypnomidate (Jassen-Cilag, Neuss, Germany) and received intraperitoneally 150 mg per kg D-luciferin (Biosynth, Staad, Switzerland) dissolved in sterile PBS. Imaging was performed with the NightOWL LB 981 system (Berthold Technologies, Bad Wildbad, Germany) with exposure times of 1 second and 20 seconds. ImageJ version 2.3 was used for color coding of signal intensity (presenting a 256 grayscale) and overlay pictures.

Statistical Analysis

All calculations and statistical analyses were performed with GraphPad Prism version 4.01. Student t test was used for comparison of only two groups. One-way analysis of variance (ANOVA) was applied for comparing the control group with several treated groups followed by Bonferroni post hoc multiple comparisons. In cell cytotoxicity assay the half-maximal effective concentration to which cell viability was reduced to 50% (EC50) values were calculated by sigmoidal dose-response curve fit of x=log(x) transformed data. Kaplan-Meier analysis was used to plot overall survival and differences in curves were analyzed by Logrank test. All tests were two-sided, and P values less than 0.05 were considered to be statistically significant. If not stated otherwise, means are reported with 95% confidence interval.

DETAILED DESCRIPTION OF THE FIGURES

Figure 1:
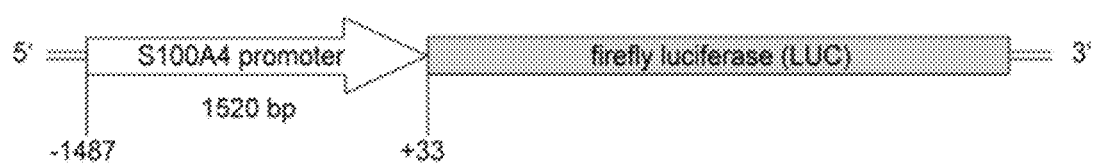
FIG. 1. Identification of niclosamide via high-throughput screening
Figure 1:
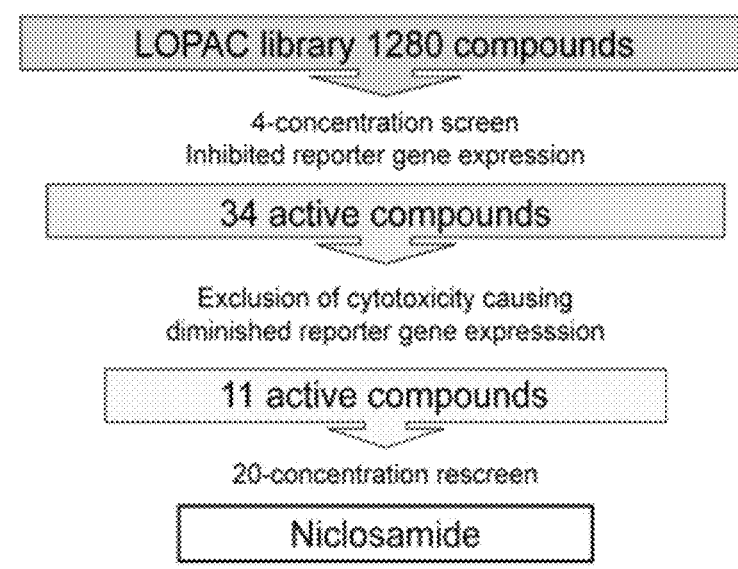
Figure 1:
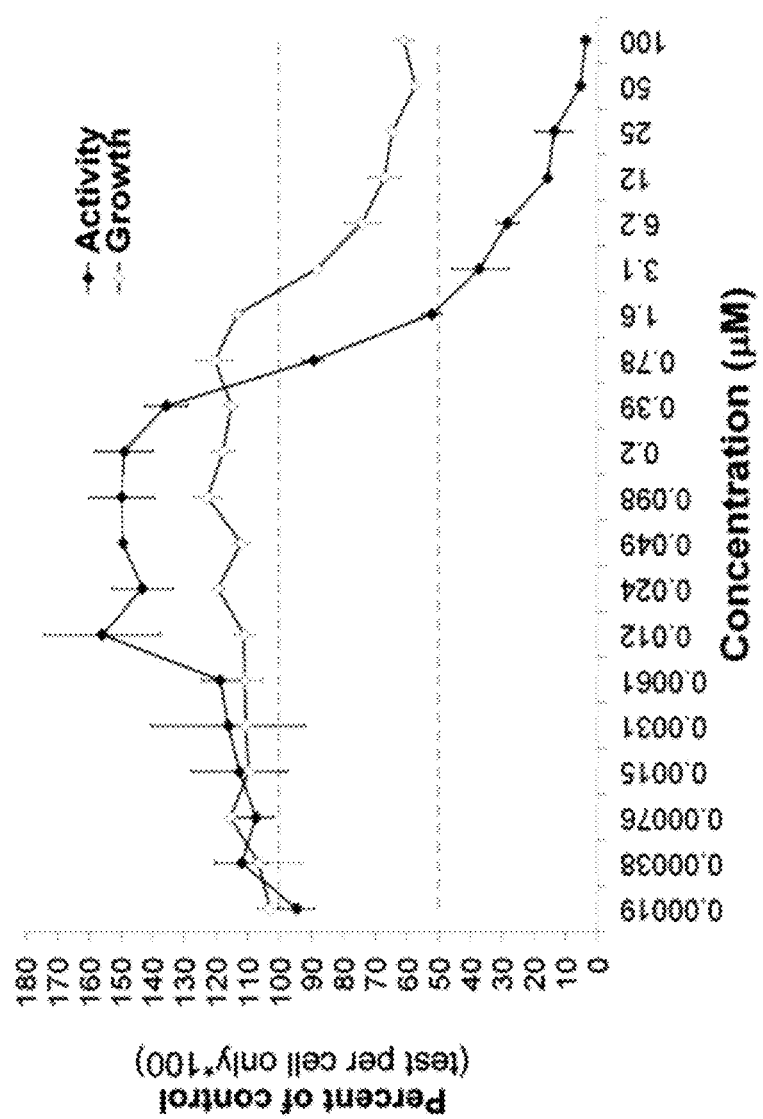

FIG. 1 Identification of Niclosamide Via High-Throughput Screening.

(A) Schematic representation of the reporter system applied in high-throughput screening. The S100A4 promoter comprising the sequence from −1487 bp upstream to the S100A4 transcription start site controlled the expression of reporter firefly luciferase (LUC). This construct was stably expressed by HCT116-S100A4p-LUC cells which were further exposed to compounds of the Library of Pharmacologically Active Compounds (LOPAC) 1280. As read out luciferase activity and cell viability was determined. (B) Schematic summary of the high throughput screening. (C) 20-concentration rescreen of niclosamide on HCT116-S100A4p-LUC cells. Cells were exposed to 20 2-fold dilutions of niclosamide in duplicate wells per dilution for 24 hours. Luciferase activity and cell viability was determined. Error bars represent the standard deviation for two duplicate wells at each dilution.

Figure 2:
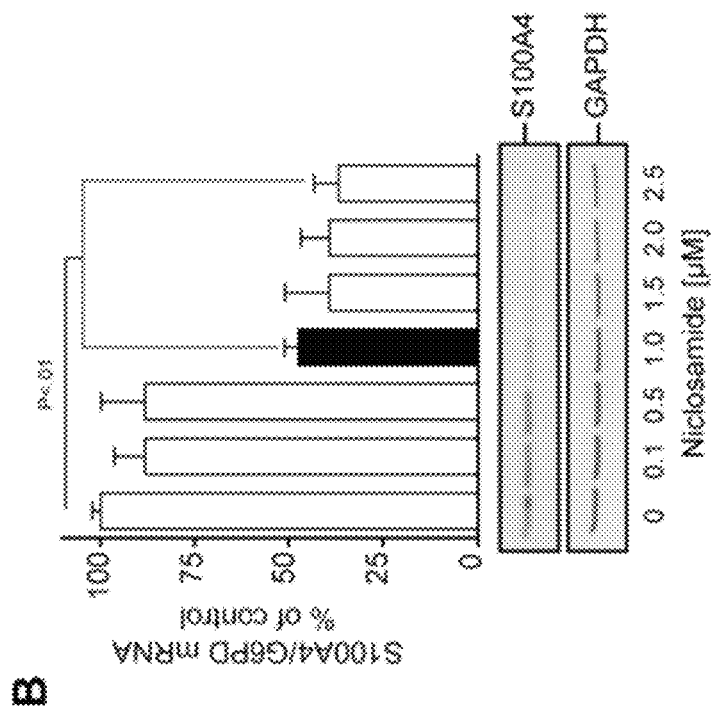
FIG. 2: Effect of niclosamide on S100A4 mRNA and protein expression in human colon cancer cells FIG. 3. Effect of niclosamide on cell motility and proliferation FIG. 4. Effect of niclosamide in SW620, LS174T, SW480, and DLD-1 colon cancer cells FIG. 5. Effect of niclosamide and its derivatives on S100A4 expression and S100A4-induced cell motility FIG. 6. Effect of niclosamide on constitutively active WNT/CTNNB1 pathway signaling FIG. 7. In vivo luminescence monitoring of niclosamide effect on metastasis in xenograft mice FIG. 8. Long-term effects of niclosamide treatment in vitro and in vivo
Figure 2:
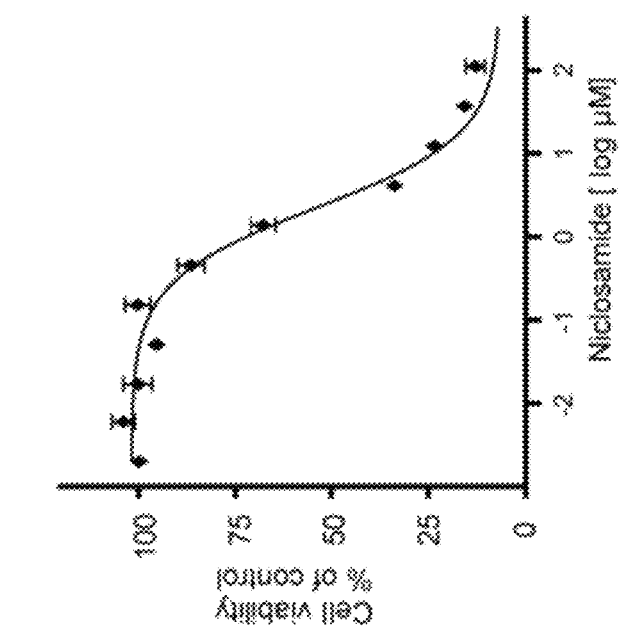
Figure 2:
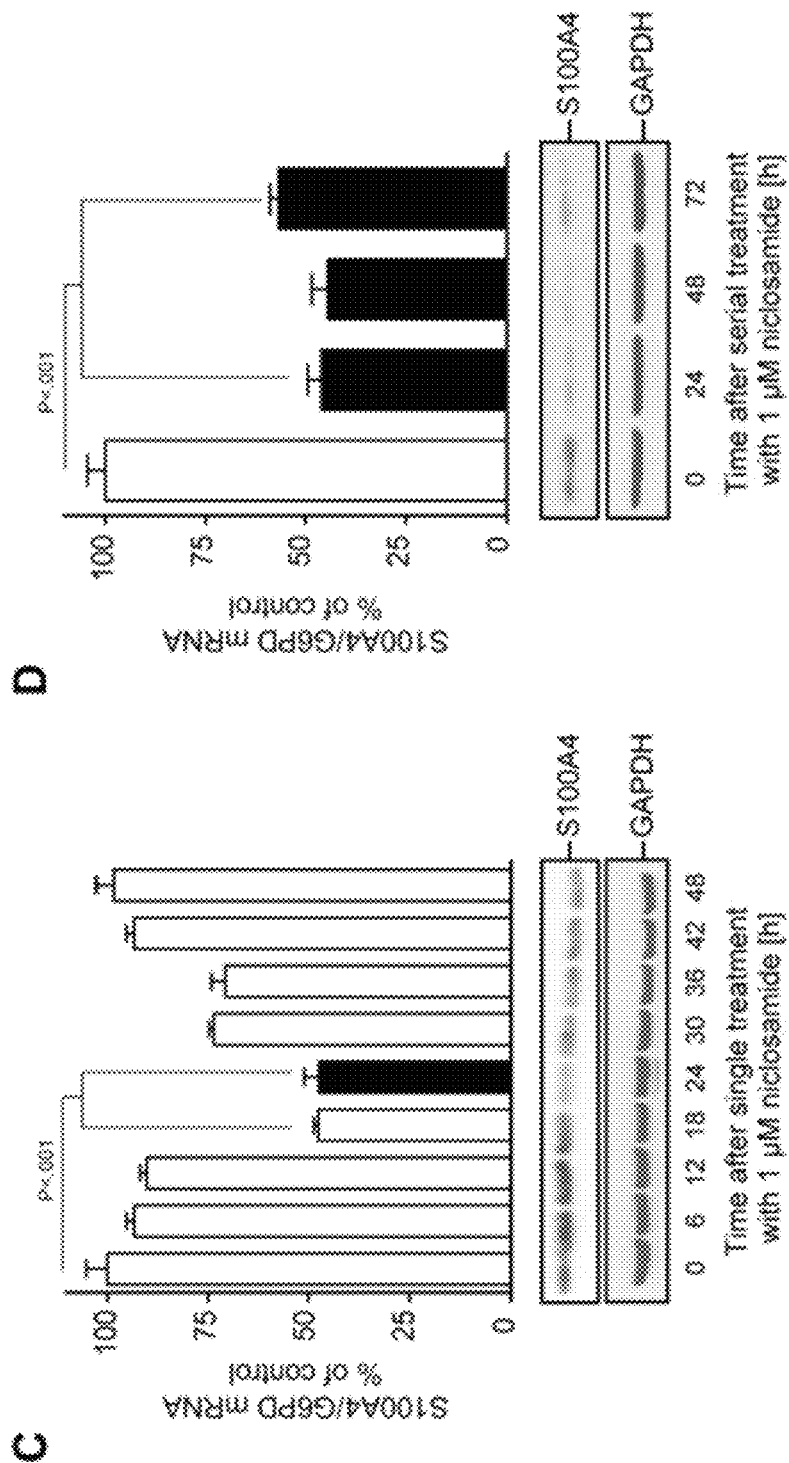
Figure 2:
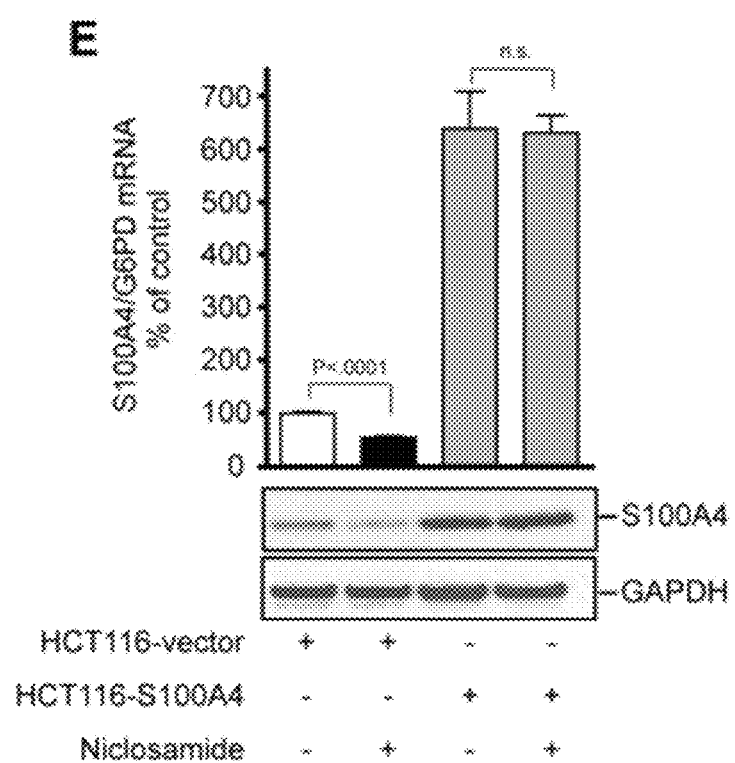

FIG. 2 Effect of Niclosamide on S100A4 mRNA and Protein Expression in Human Colon Cancer Cells.

(A) Determination of the cytotoxicity of niclosamide on HCT116 cells. Cells were treated with increasing concentrations of niclosamide for 24 hours and cell viability was measured. (B) Effect of increasing concentrations of niclosamide on S100A4 expression. HCT116 cells were treated with increasing concentrations of niclosamide for 24 hours. S100A4 expression was determined by quantitative reverse-transcription-polymerase chain reaction (qRT-PCR) and immunoblot. (C) Time-dependency of niclosamide effect on S100A4 expression. HCT116 cells were treated with a single dose of 1 μM niclosamide for 24 hours and S100A4 expression was analyzed by qRT-PCR and immunoblot at indicated time points. Black bar indicates the chosen treatment conditions for further experiments. (D) Effect of daily doses of niclosamide on S100A4 expression. HCT116 cells were treated daily with 1 μM niclosamide and S100A4 expression was analyzed by qRT-PCR and immunoblot. Data is given as mean±SD (n>2). Differences in treated groups were compared with the control group by two-sided one-way analysis of variances and Bonferroni post hoc multiple comparison test.

(E) Effect of niclosamide in HCT116-vector and HCT116-S100A4 cells. HCT116-vector and HCT116-S100A4 cells were treated with 1 µM niclosamide for 24 hours and S100A4 expression was analyzed by qRT-PCR and immunoblot. Data is given as mean±SD (n>2). Comparison of niclosamide vs. solvent-treated cells was analyzed with Student's t test.

Figure 3:
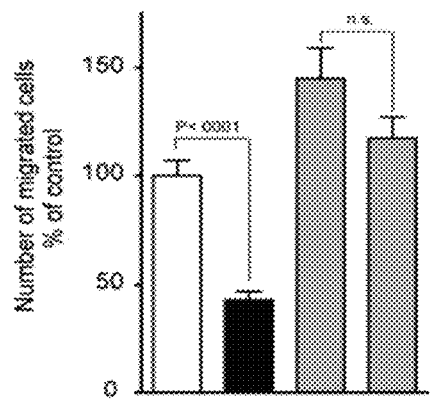
Figure 3:
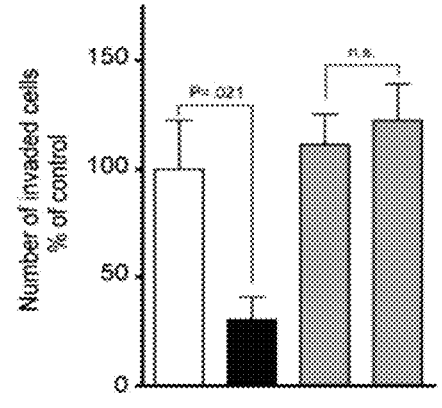
Figure 3:
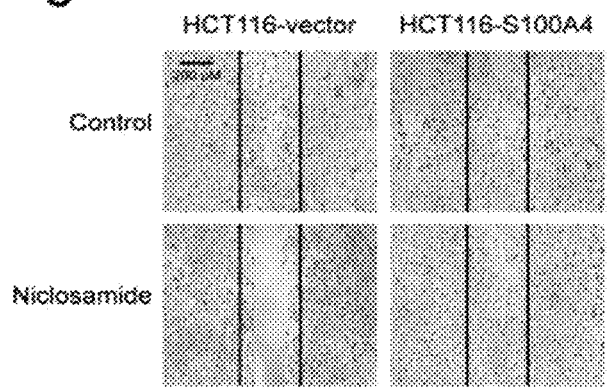
Figure 3:
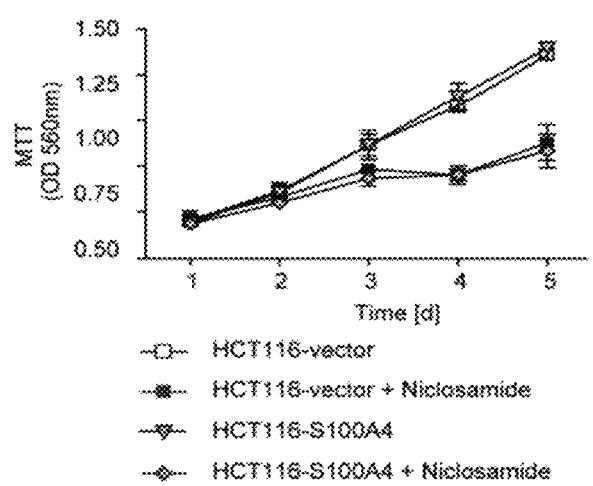
Figure 3:
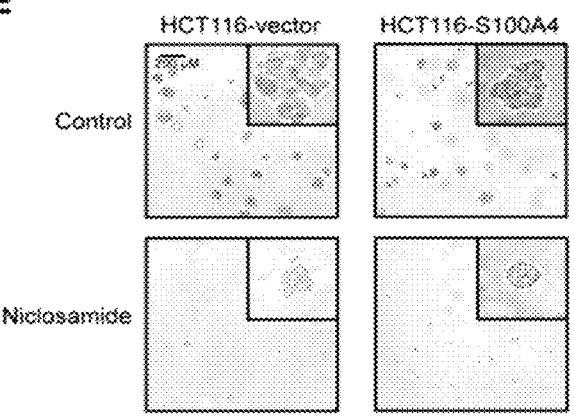
Figure 3:
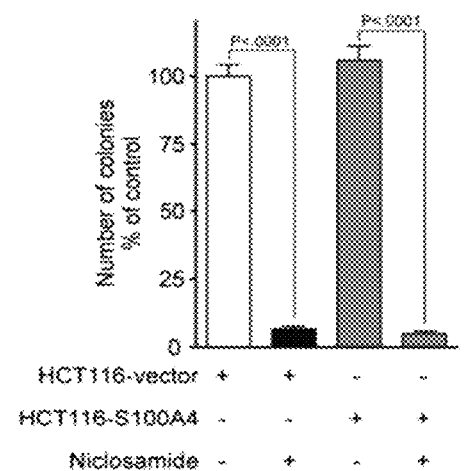

FIG. 3 Effect of Niclosamide on Cell Motility and Proliferation.

(A) Cell migration of HCT116-vector and HCT116-S100A4 cells exposed to niclosamide treatment. Cells were treated with 1 µM niclosamide for 24 hours and migration rates were measured with Boyden chamber assay. (B) Cell invasion of HCT116-vector and HCT116-S100A4 cells exposed to niclosamide treatment. Cells were treated with 1 µM niclosamide for 24 hours and cell invasion was determined by Boyden chamber assay. (C) Directed migration of HCT116-vector and HCT116-S100A4 cells exposed to niclosamide treatment analyzed by wound healing assay. Wounds of 300 µM width were set in a 60% confluent monolayer of HCT116-vector or HCT116-S100A4 cells on day 1. Cells were treated daily with 1 µM niclosamide for 4 days. Microphotographs of day 4 are presented here with black lines indicating margins of entered wound of day 1; scale bar represents 200 µM. Data represents three independent experiments. (D) Adhesive cell proliferation of HCT116-vector and HCT116-S100A4 cells exposed to niclosamide treatment. Cells were treated daily with 1 µM niclosamide and cell viability was determined with MTT assay. (E) Anchorage-independent cell growth of HCT116-vector and HCT116-S100A4 cells exposed to niclosamide treatment. Cells were plated as single cells into 0.33% (w/v) agarose and treatment (solvent or 1 µM niclosamide) containing medium. After 7 days colonies were visualized by light microscopy at 10× (overview) and 40× (single colony) magnification. (F) Quantification of colonies formed. Number of colonies (of more than 4 cells) was counted and normalized to solvent-treated HCT116-vector cells. Differences of niclosamide vs. solvent-treated cells were analyzed by Student's t test. Data represent mean±SE (n>2) of at least two independent experiments each performed in at least duplicate.

Figure 4:
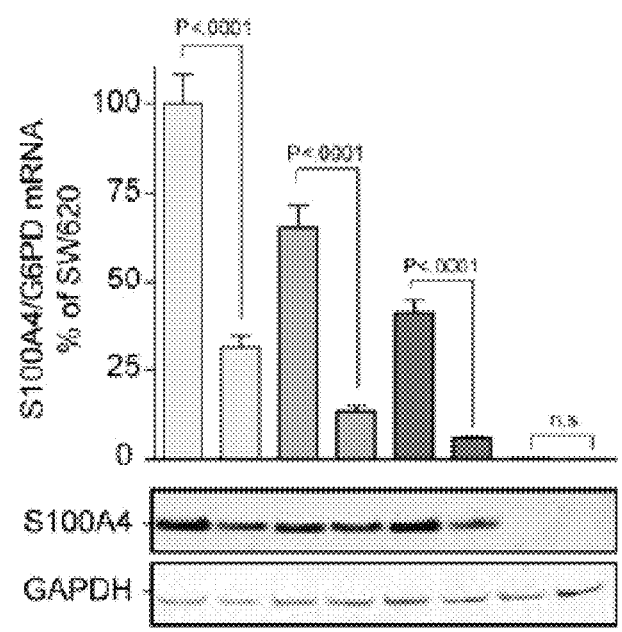
Figure 4:
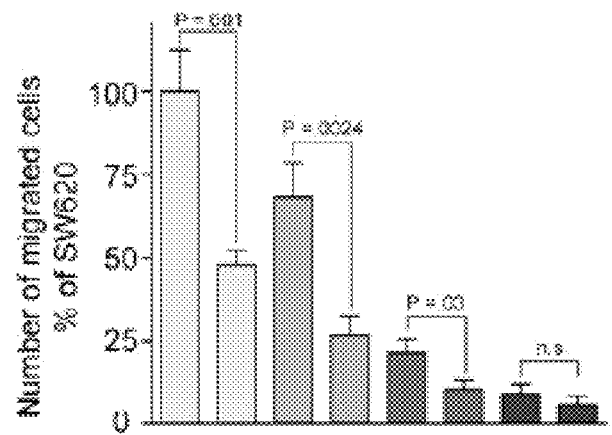
Figure 4:
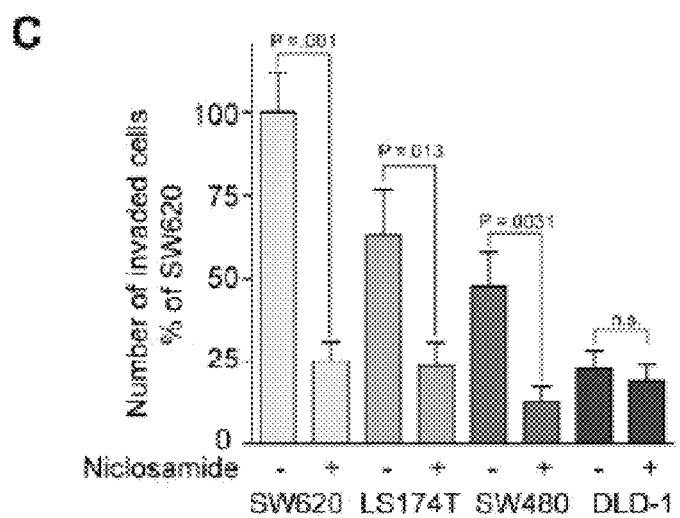
Figure 4:
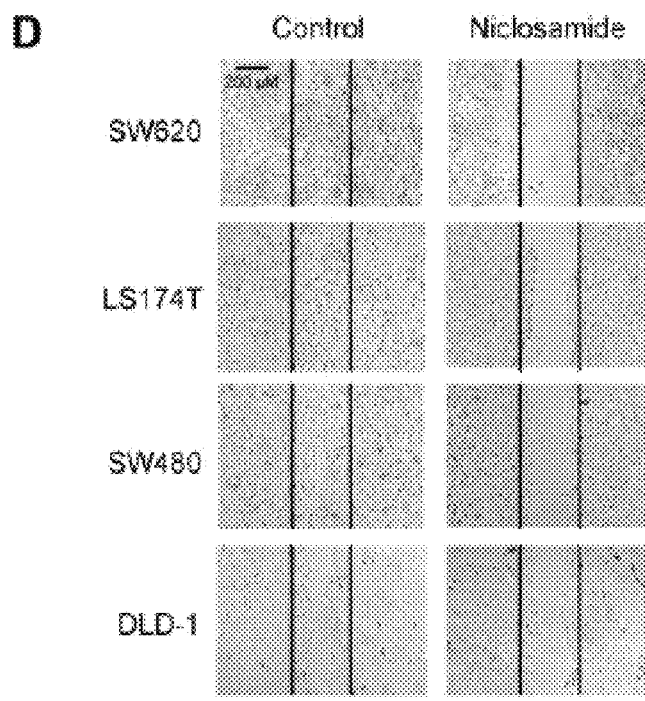
Figure 4:
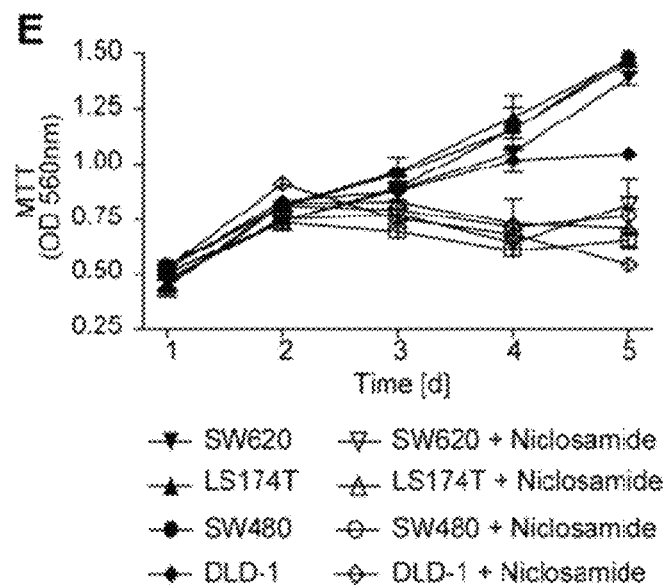
Figure 4:
Figure 4:
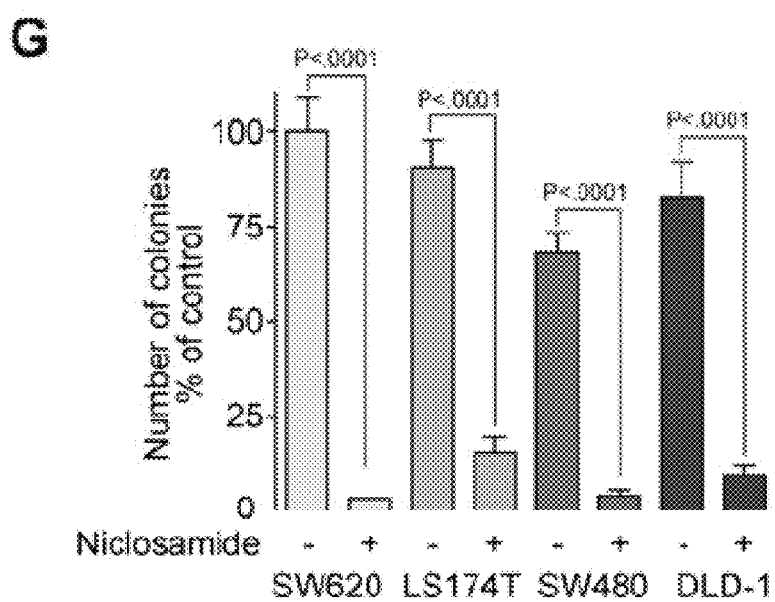

FIG. 4 Effect of Niclosamide in SW620, LS174T, SW480, and DLD-1 Colon Cancer Cells.

(A) S100A4 expression under niclosamide treatment. Cells were treated with 1 µM niclosamide for 24 hours. S100A4 expression was analyzed with qRT-PCR and immunoblot. (B) Cell migration under niclosamide treatment. Migration rates of cells treated with 1 µM niclosamide for 24 hours were determined in a Boyden chamber assay values were normalized to solvent-treated SW620 cells. (C) Cell invasion under niclosamide treatment. Cells were seeded onto Matrigel covered transwells and treated with 1 µM niclosamide for 24 hours. Invaded cells in the lower chamber were counted and normalized to solvent-treated SW620 cells. Differences in solvent vs. niclosamide-treated cells were analyzed by Student's t test. Data represent mean±SE of at least two independent experiments each performed in triplicate. (D) Directed migration under niclosamide treatment. Wounds of 300 µM width were set in a 60% confluent monolayer of cells on day 1. Cells were treated daily with 1 µM niclosamide for 4 days. Microphotographs of day 4 are presented here with black lines indicating margins of the wound on day 1; scale bar represents 200 µM. Directed migration data shown are representatives of three independent experiments. (E) Adhesive cell proliferation under niclosamide treatment. Cells were treated daily with 1 µM niclosamide. The amount of viable cells per well was determined by MTT assay. (F) Anchorage-independent cell growth under niclosamide treatment. Cells were plated as single cells into 0.33% (w/v) agarose and treatment (solvent or 1 µM niclosamide) containing medium. After 7 days colonies were visualized by light microscopy at 10× (overview) and 40× (single colony) magnification. (G) Quantification of colonies formed. Number of colonies (of more than 4 cells) was counted and normalized to solvent-treated SW620 cells. Differences in solvent vs. niclosamide-treated cells were analyzed by Student's t test. Data represent mean mean±SE of at least two independent experiments each performed in duplicates.

Figure 5:
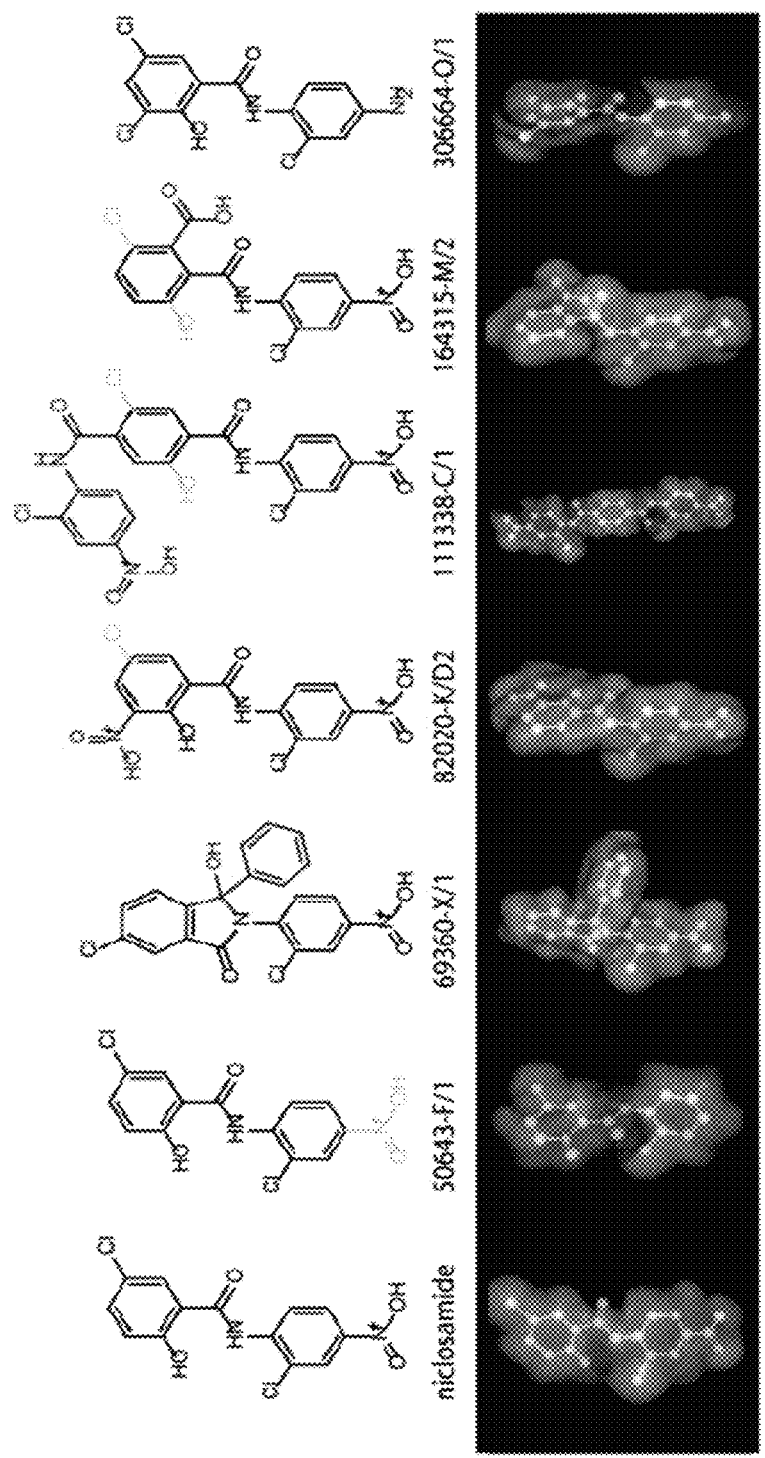
Figure 5:
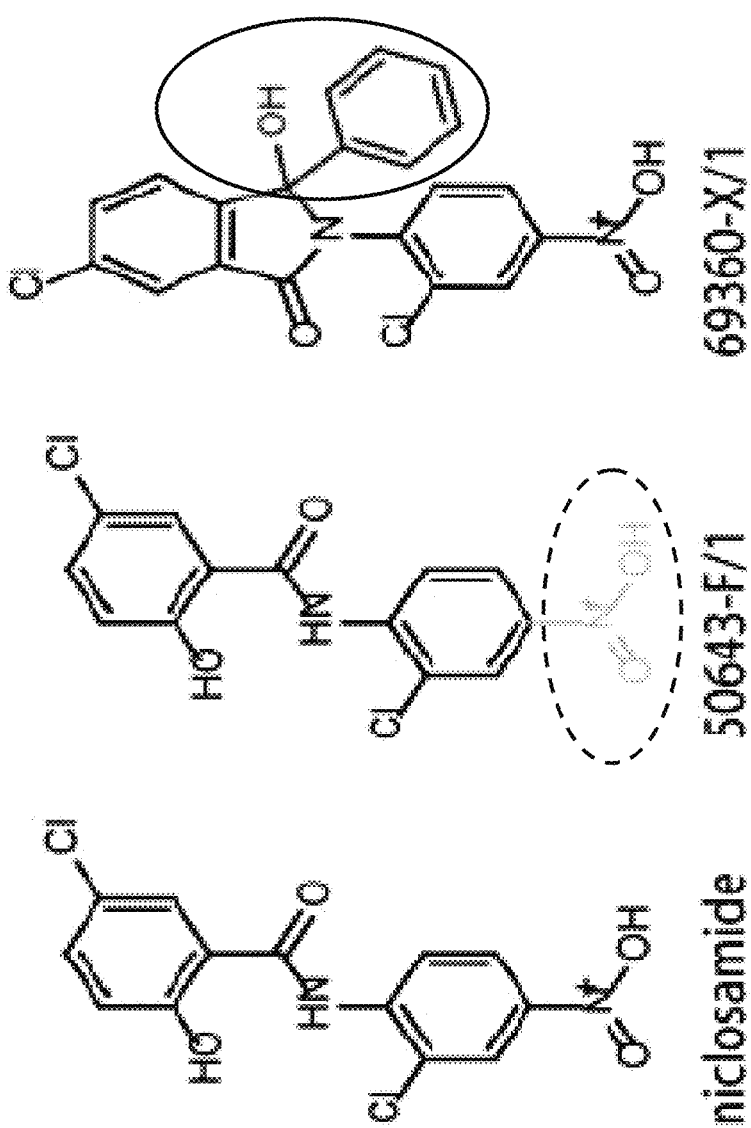
Figure 5:
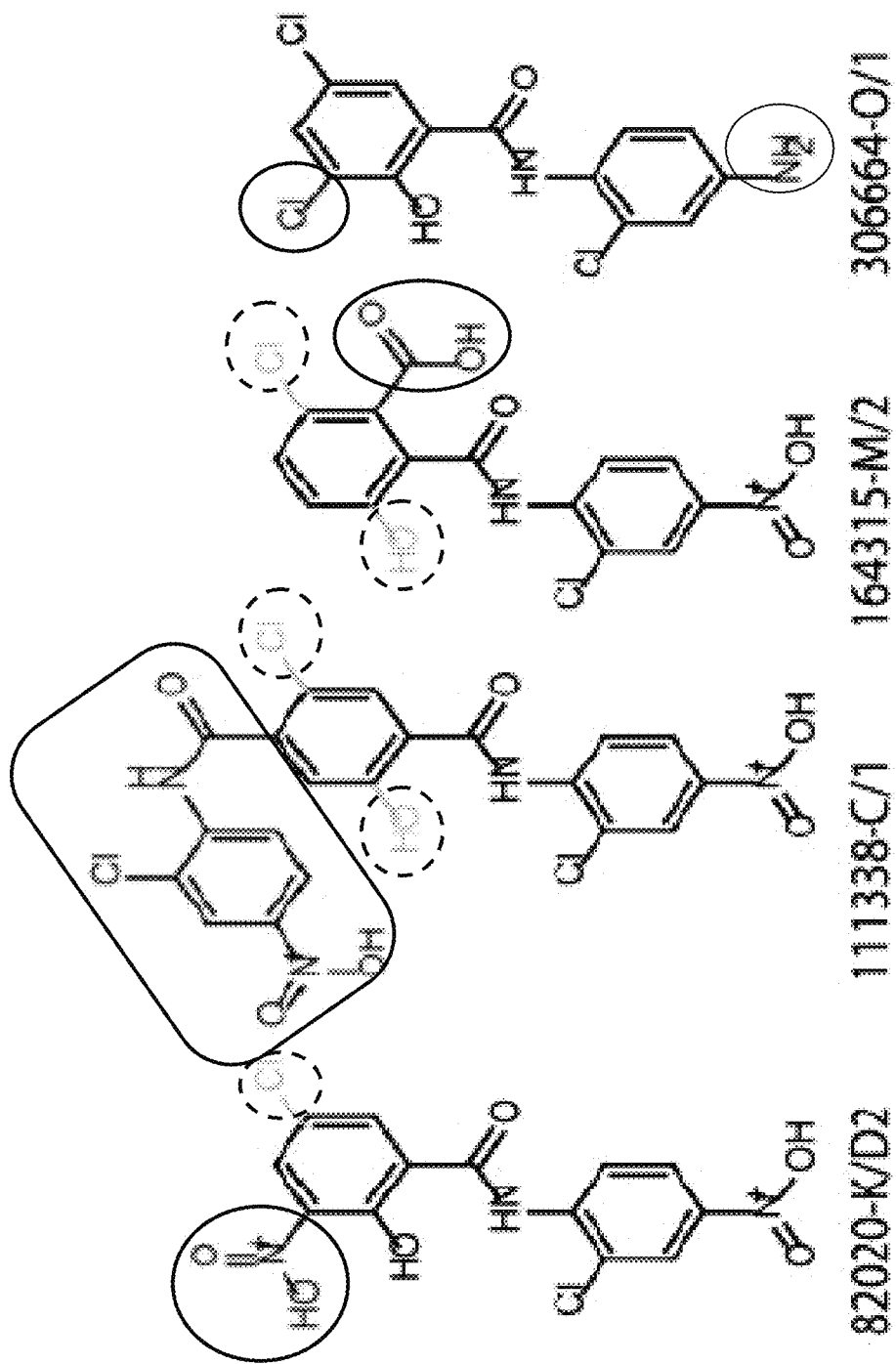
Figure 5:
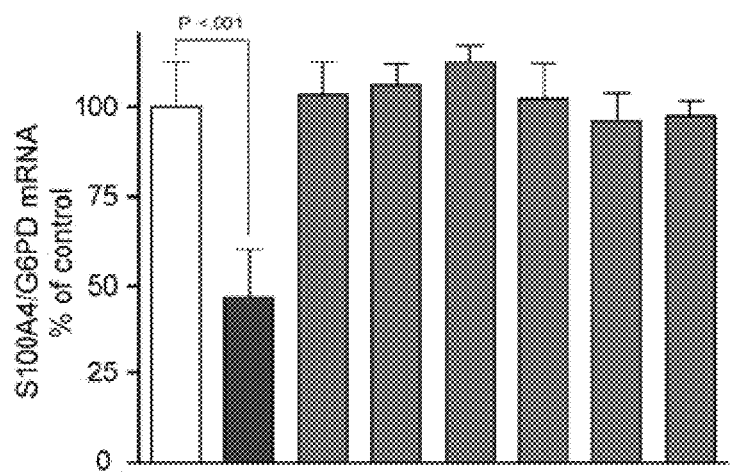
Figure 5:
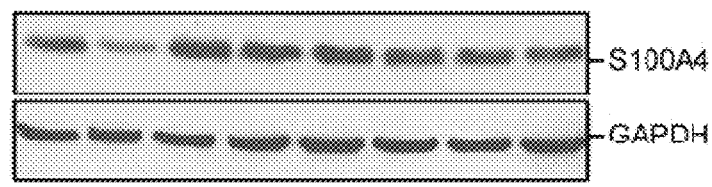
Figure 5:
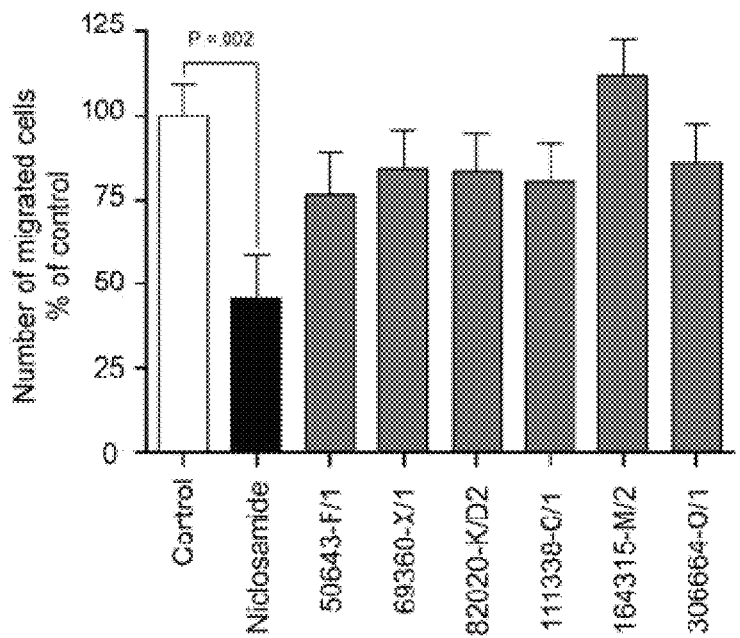

FIG. 5 Effect of Niclosamide and its Derivatives on S100A4 Expression and S100A4-Induced Cell Motility.

(A) Chemical structure of niclosamide and its derivatives. In 2D illustrations the niclosamide structure was compared with the structure of niclosamide derivatives; marked in solid circles or boxes are added chemical groups, marked in grey and surrounded by dotted lines are removed chemical groups. In 3D illustrations grey clouds represent van der Waals surface, red and blue indicate negative and positive charges, respectively. (B) S100A4 expression under treated conditions. HCT116 cells were treated with 1 µM niclosamide or one of the niclosamide derivatives for 24 hours. S100A4 expression was analyzed by qRT-PCR and immunoblot. (C) Cell migration under treated conditions. HCT116 cells were treated with 1 µM niclosamide or one of its derivatives for 24 hours and cell migration was determined by Boyden chambder assay. Cells migrated to the lower chamber were counted and normalized to the number of migrated, solvent-treated HCT116 cells. Comparison of niclosamide or derivative-treated vs. solvent-treated cells was performed by two-sided one-way analysis of variance and Bonferroni post hoc multiple comparison test. Data is given as mean±SE at least four independent experiments each performed in duplicates.

Figure 6:
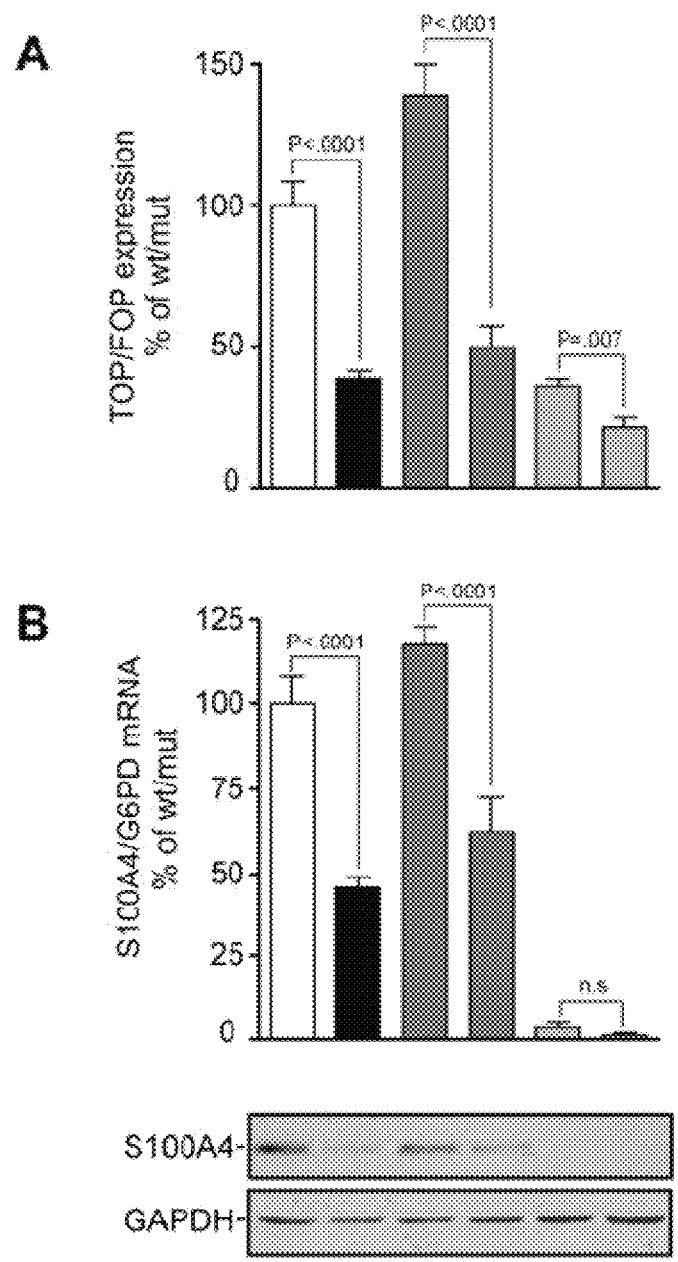
Figure 6:
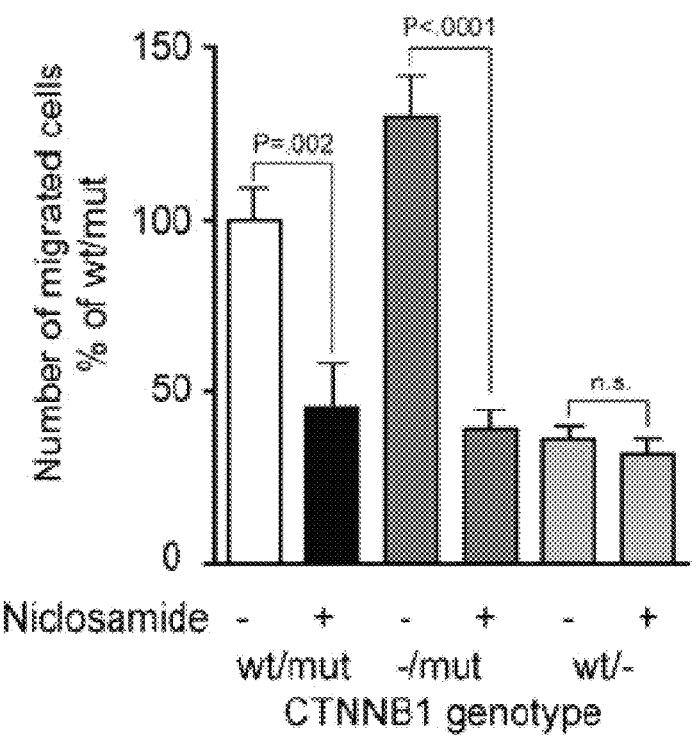
Figure 6:
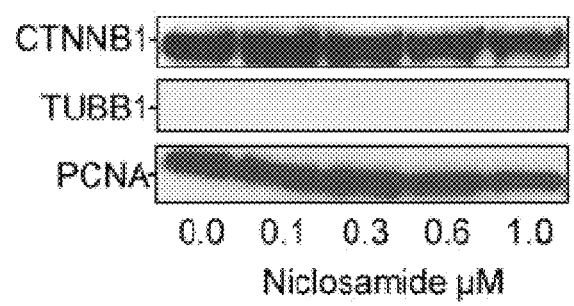
Figure 6:
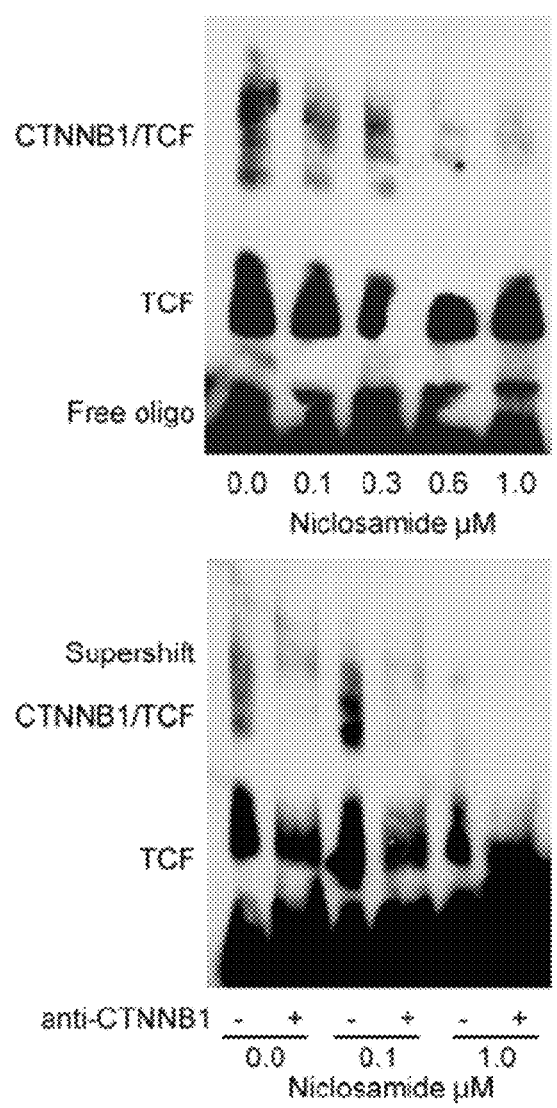
Figure 6:
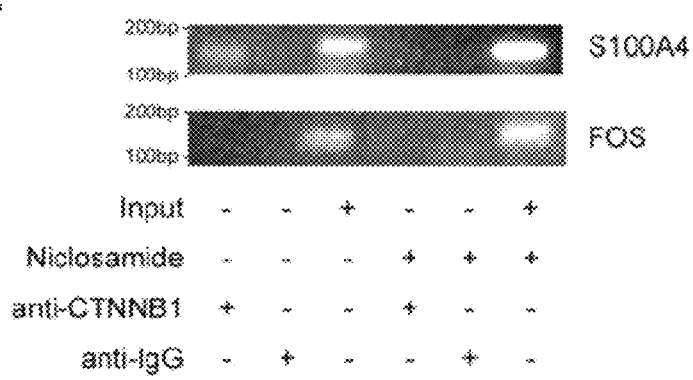

FIG. 6 Effect of Niclosamide on Constitutively Active WNT/CTNNB1 Pathway Signaling.

For WNT pathway analysis the following cells were applied: HCT116 cells (heterozygous for gain-of-function-mutated CTNNB1; wt/mut), HAB-68mut cells (deletion mutant of HCT116, expressing only gain-of-function-mutated CTNNB1: −/mut) and HAB-92 wt cells (deletion mutant of HCT116, expressing only wild-type CTNNB1: wt/−). (A) CTNNB1 genotype dependent effect of niclosamide on LEF/TCF transcription factor reporter gene expression. Cells were treated with 1 µM niclosamide for 24 hours. Reporter gene expression was determined by luciferase activity measurement. For each condition and cell line TOPflash expression was normalized to FOPflash expression. (B) CTNNB1 genotype dependent effect of niclosamide on S100A4 expression. Cells were treated with 1 µM niclosamide for 24 hours. S100A4 expression was analyzed by qRT-PCR and immunoblot. (C) CTNNB1 genotype dependent effect of niclosamide on migration rates. Cells were treated with 1 µM niclosamide for 24 hours and cell migration was determined by Boyden chamber assay. Data represents mean±SE of at least three independent experiments. Differences were analyzed by Student's t test (n.s.; not statistically significant). (D) Nuclear localization of CTNNB1 under niclosamide treatment. Nuclear extracts of HCT116 cells treated with the indicated concentrations of niclosamide for 18 hours were analyzed by immunoblot. (E)

Effect of niclosamide on CTNNB1/TCF complex. Nuclear extracts of HCT116 cells treated with the indicated concentrations of niclosamide for 18 hours were analyzed by EMSA for the TCF-binding site of the S100A4 promoter. Supershift was performed by addition of a monoclonal anti-CTNNB1 antibody. (F) Presence of CTNNB1 on the S100A4 promoter under niclosamide treatment. HCT116 cells were treated with 1 μM niclosamide for 18 hours and processed for ChIP assay. Soluble chromatin was immunoprecipitated with a monoclonal anti-CTNNB1 antibody or a nonspecific control IgG antibody. Primers used in PCR amplified a 167 bp fragment of the S100A4 promoter or 149 bp fragment of the FOS promoter. The input verified the integrity of the PCR. The FOS promoter sequence to which CTNNB1 does not bind was used as control. Data shown are representatives of at least two independent experiments.

Figure 7:
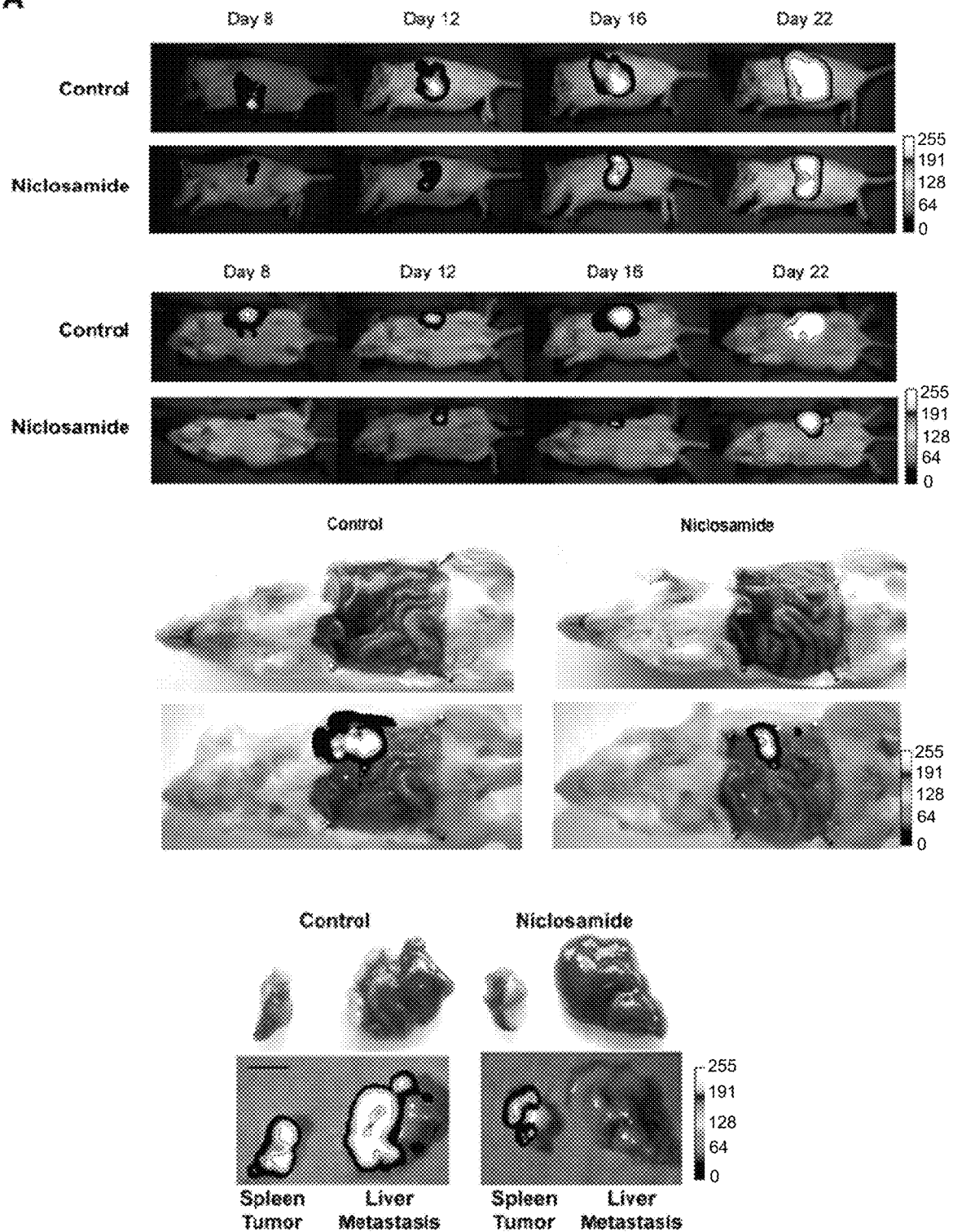
Figure 7:
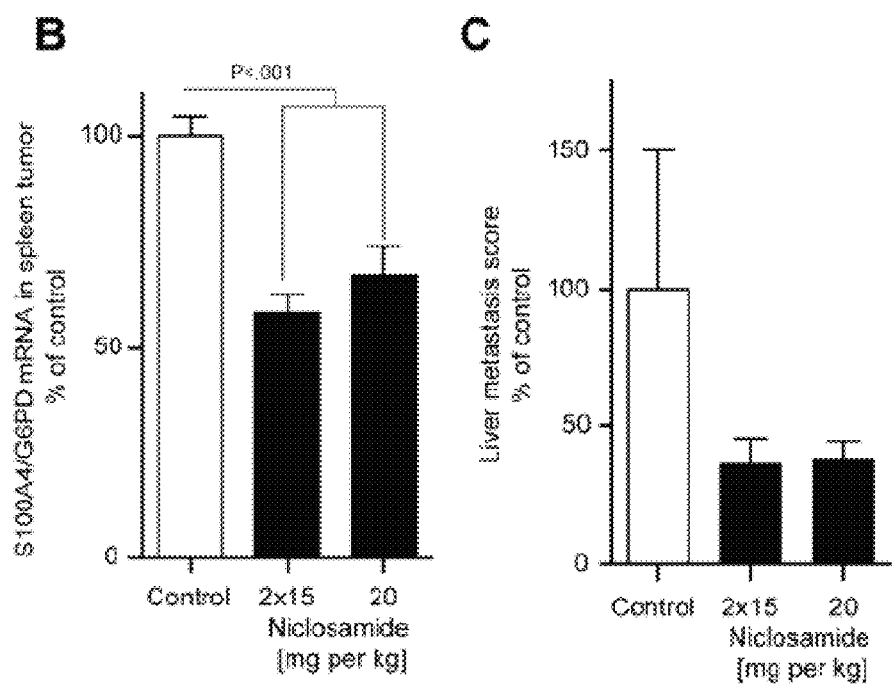

FIG. 7 In Vivo Luminescence Monitoring of Niclosamide Effect on Metastasis in Xenograft Mice.

(A) In vivo luminescence imaging of metastasis under niclosamide treatment. HCT116-CMVp-LUC cells stably expressing firefly luciferase (LUC) were intrasplenically transplanted into mice (per group n=4) followed by daily intraperitoneal treatment with 20 mg per kg niclosamide. For luminescence imaging, mice were anesthetized at the indicated days and received intraperitoneally D-luciferin. Exposure time for lateral and ventral imaging was 20 seconds per picture. In situ imaging and imaging of isolated organs was performed for 1 second per picture exposure time. Signal intensity of grayscale images (256 scale) were color coded (from low to high signal intensity: blue, green, yellow, red, white) and overlayed with bright field picture. (B) S100A4 mRNA level in spleen tumor of niclosamide-treated xenograft mice. Spleens from mice (per group n=9) were dissected on day 24. Tumor tissue was cryosected for RNA isolation. S100A4 mRNA level was measured by qRT-PCR and expressed as percentage of control mice. Differences were analyzed by two-sided one-way analysis of variance and Bonferroni post hoc multiple comparison test. Bars represent mean±SD. (C) Liver metastases size in niclosamide-treated xenograft mice. Liver was dissected from xenograft mice (per group n=9) intraperitoneally treated twice per day with 15 mg per kg or daily with 20 mg per kg niclosamide for 24 days. Metastasis was quantified by scoring. Data is given as mean±SD.

Figure 8:
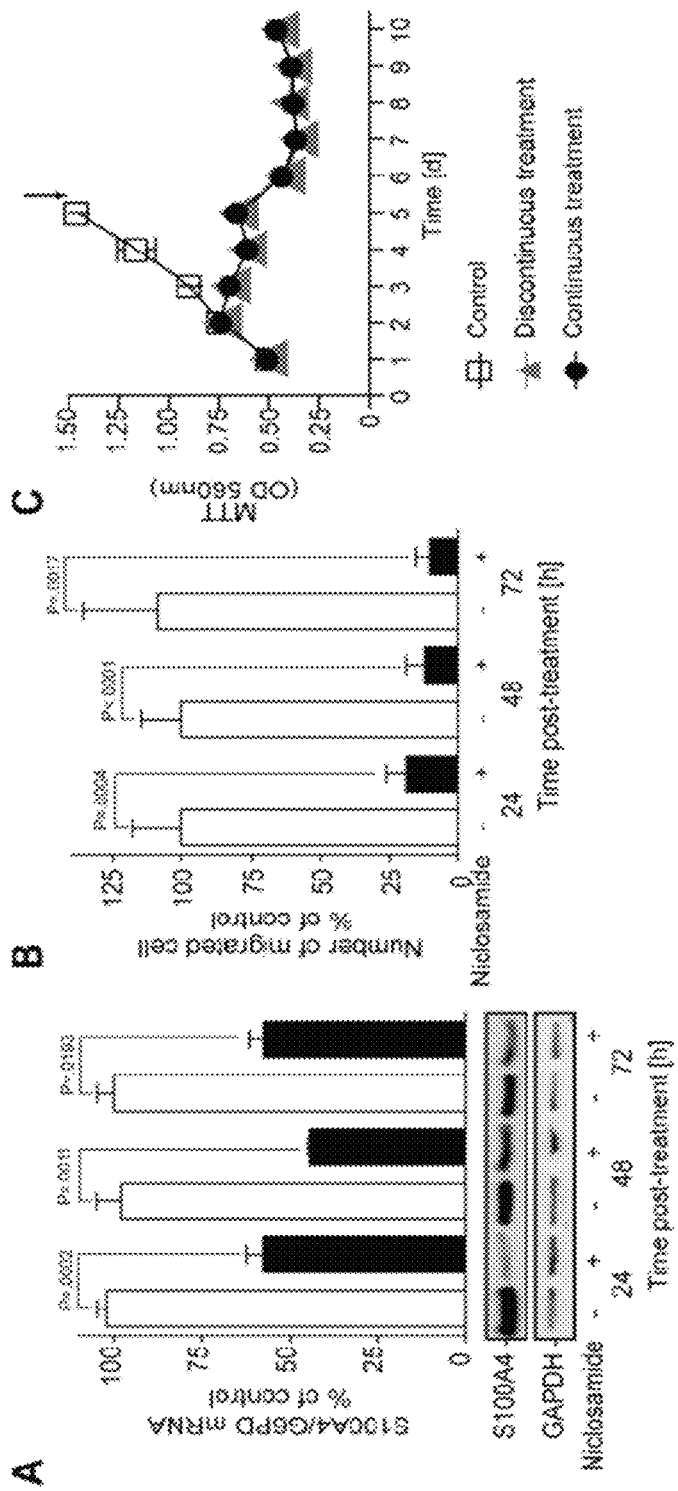
Figure 8:
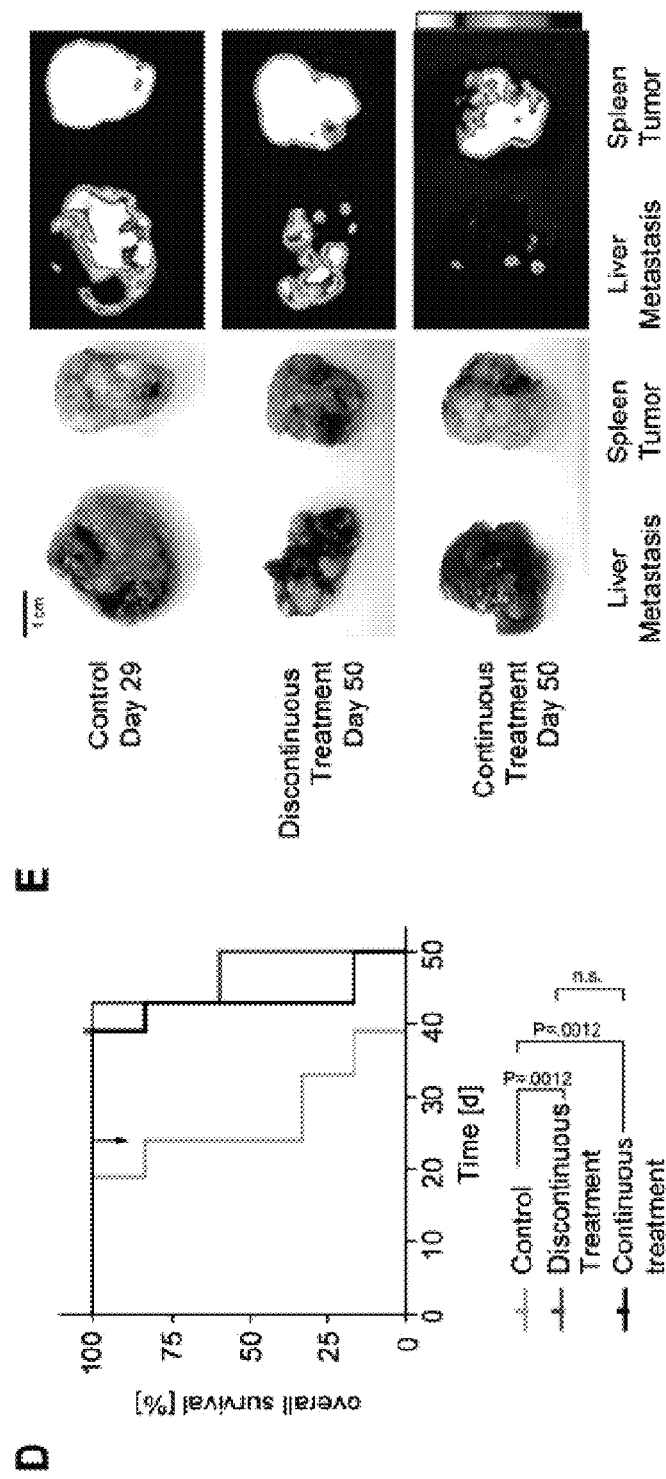
Figure 8:
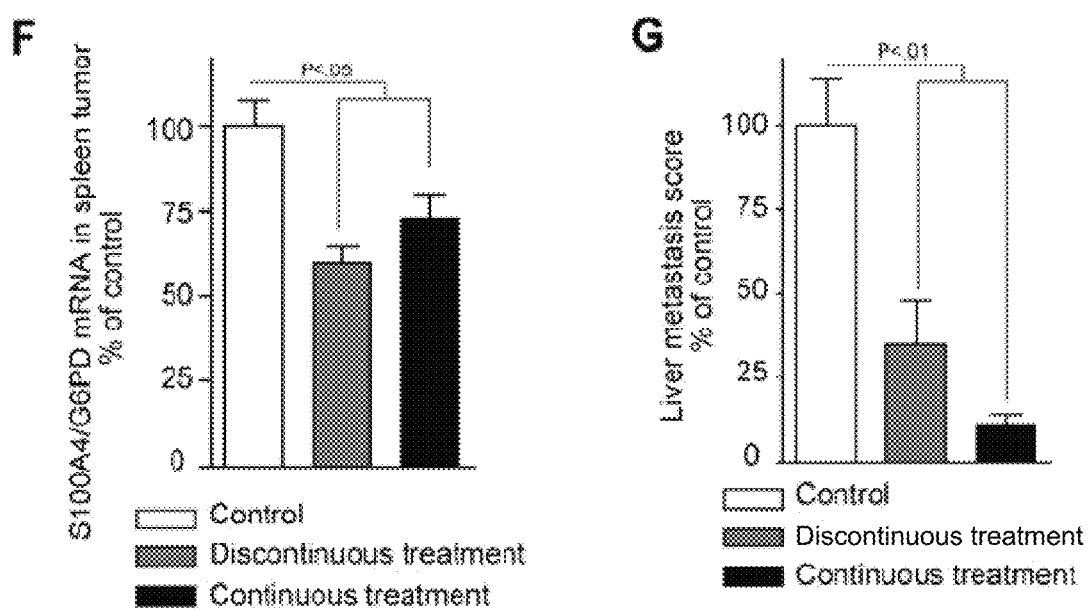

FIG. 8 Long-Term Effects of Niclosamide Treatment In Vitro and In Vivo.

(A) S100A4 expression in vitro after discontinued niclosamide treatment. HCT116 cells were treated daily with 1 μM niclosamide for three consecutive days, medium was removed on day 4, and S100A4 expression was analyzed 24, 48, and 72 hours after niclosamide removal. S100A4 expression was analyzed by qRT-PCR and immunoblot. (B) Cell migration after discontinued niclosamide treatment. Cell migration rates of HCT116 cells treated as in (A) were determined by Boyden chamber assay. Differences in control vs. treated cells were analyzed by Student's t test. (C) Anchorage-dependent cell proliferation after discontinued niclosamide treatment. HCT116 cells were treated with 1 μM niclosamide or solvent daily, or niclosamide for the first five days and solvent from day 5 on (arrow indicates discontinuation of treatment). Cell proliferation was determined by MTT assay. (D) Overall-survival of continuously and discontinuously niclosamide-treated mice. HCT116-CMVp-LUC cells were intrasplenically injected into mice (per group n=6). Mice were daily treated intraperitoneally with either solvent or 20 mg per kg niclosamide, or for the first 24 days with 20 mg per kg niclosamide followed by solvent. Comparison of survival curves was performed by logrank test. (E) Luminescence signal from liver metastases and spleen tumors. Mice were intraperitoneally injected with D-luciferin 10 minutes before liver and spleen were dissected and imaged for 1 second exposure. Signal intensity of grayscale images (256 scale) were color coded with white as the highest signal intensity. (F) S100A4 mRNA expression in spleen tumors. Tumor tissue was cryosected for RNA isolation. S100A4 mRNA level was measured by qRT-PCR and expressed as percentage of control animals. (G) Size of liver metastases in continuously and discontinuously niclosamide-treated mice. Liver metastases on dissected livers were quantified by scoring. Bars represent mean±SE. Differences were analyzed by two-sided one-way analysis of variance and Bonferroni post hoc multiple comparison tests.

What is claimed is:

1. A method of reducing or inhibiting expression level of S100A4 in cancer cells in a subject, comprising:
   identifying the subject as having a cancer with cancer cells having an elevated or up-regulated level of S100A4 expression compared to a level of S100A4 expression in non-oncogenic cells in the subject, and
   administering to the subject a therapeutically effective amount of niclosamide, thereby inhibiting or reducing S100A4 expression in the cancer cells,
   wherein 15 to 400 mg niclosamide is administered per kg body weight of the subject (mg/kg), 1 or 2 times daily,
   wherein the inhibited or reduced expression level of S100A4 reduces S100A4-induced motility of the cancer cells.

2. The method according to claim 1, wherein the niclosamide is administered orally.

3. The method according to claim 1, wherein the niclosamide is administered intraperitoneally.

4. The method according to claim 1, wherein 15 to 200 mg niclosamide is administered per kg body weight of the subject (mg/kg), 1 or 2 times daily.

5. The method according to claim 4, wherein 20 to 200 mg niclosamide is administered per kg body weight of the subject (mg/kg), once daily.

6. The method according to claim 1, wherein the subject is a human subject.

7. The method according to claim 1, comprising the inhibition and/or reduction of cancer cell motility.

8. The method according to claim 1, comprising the inhibition and/or reduction of cancer cell migration and invasion.

9. The method according to claim 1, wherein the cancer is selected from the group consisting of colon cancer, breast cancer, ovarian carcinoma, osteosarcoma, cervical cancer, prostate cancer, lung cancer, synovial carcinoma, melanoma, skin and pancreatic cancer.

10. The method according to claim 1, wherein the cancer is colon cancer.

11. The method according to claim 1, wherein 20 to 200 mg niclosamide is administered per kg body weight of the subject (mg/kg), once daily, and wherein the cancer is colon cancer.

12. The method according to claim 1, wherein a body fluid and/or a tissue of a patient to be identified is analyzed to determine S100A4 expression levels.

13. The method according to claim 1, comprising the administration of a pharmaceutical composition comprising at least one niclosamide or with a pharmaceutically acceptable carrier, wherein said composition is a tablet, a coated tablet, a capsule, a suppository, an ointment, a cream, an injection solution and/or an infusion solution.

14. The method according to claim 13, comprising the administration of a pharmaceutical composition, wherein the composition comprises niclosamide and one or more additional chemotherapeutic agents.

15. The method according to claim 13, wherein the body fluid and/or the tissue of the patient to be identified is analyzed to determine S100A4 transcription levels.

* * * * *